United States Patent
Blackmon

(10) Patent No.: US 12,053,022 B2
(45) Date of Patent: Aug. 6, 2024

(54) CAPSULES WITH INTEGRATED MOUTHPIECES, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventor: Zack W. Blackmon, Williamsburg, VA (US)

(73) Assignee: Altria Client Services LLC, Richmond, VA (US)

( * ) Notice: Subject to any disclaimer, the term of this patent is extended or adjusted under 35 U.S.C. 154(b) by 598 days.

(21) Appl. No.: 17/140,215

(22) Filed: Jan. 4, 2021

(65) Prior Publication Data

US 2022/0211106 A1    Jul. 7, 2022

(51) Int. Cl.
*A24F 40/42*     (2020.01)
*A24F 40/20*     (2020.01)
(Continued)

(52) U.S. Cl.
CPC .............. *A24F 40/42* (2020.01); *A24F 40/20* (2020.01); *A24F 40/46* (2020.01); *A24F 40/465* (2020.01)

(58) Field of Classification Search
CPC ..................................................... A24F 40/20
See application file for complete search history.

(56) References Cited

U.S. PATENT DOCUMENTS

| | | |
|---|---|---|
| 855,984 A | 6/1907 | Russell |
| 1,071,389 A | 8/1913 | Blosser |

(Continued)

FOREIGN PATENT DOCUMENTS

| | | |
|---|---|---|
| CN | 103945716 A | 7/2014 |
| CN | 203986136 U | 12/2014 |

(Continued)

OTHER PUBLICATIONS

International Preliminary Report on Patentability and Written Opinion thereof dated Jul. 13, 2023 for corresponding International Application No. PCT/US2021/060505.

(Continued)

*Primary Examiner* — Christopher M Rodd
*Assistant Examiner* — Daniel Edward Vakili
(74) *Attorney, Agent, or Firm* — Harness, Dickey & Pierce, P.L.C.

(57) ABSTRACT

A capsule for a heat-not-burn (HNB) aerosol-generating device may include a base portion, a first cover, a second cover, an aerosol-forming substrate, and a heater. The base portion includes an engagement assembly configured to couple with the first cover and the second cover. The first cover defines a first recess, and the second cover defines a second recess. When assembled, the first cover is aligned with the second cover such that the first recess and the second recess collectively form a chamber. The aerosol-forming substrate is within the chamber. The heater is configured to heat the aerosol-forming substrate to generate an aerosol. The heater includes a first end section, an intermediate section, and a second end section. The heater extends through the base portion such that the intermediate section is in the chamber, while the first end section and the second end section are external segments.

22 Claims, 18 Drawing Sheets

(51) Int. Cl.
*A24F 40/46* (2020.01)
*A24F 40/465* (2020.01)

(56) References Cited

U.S. PATENT DOCUMENTS

| | | |
|---|---|---|
| 1,934,887 A | 11/1933 | Robinson |
| 4,214,146 A | 7/1980 | Schimanski |
| 4,564,748 A | 1/1986 | Gupton |
| 4,947,874 A | 8/1990 | Brooks et al. |
| 5,388,572 A | 2/1995 | Mulhauser et al. |
| 5,388,573 A | 2/1995 | Mulhauser et al. |
| 5,441,060 A | 8/1995 | Rose et al. |
| 5,460,173 A | 10/1995 | Mulhauser et al. |
| 5,593,792 A | 1/1997 | Farrier et al. |
| 5,619,984 A | 4/1997 | Hodson et al. |
| 5,645,050 A | 7/1997 | Zierenberg et al. |
| 5,665,262 A | 9/1997 | Hajaligol et al. |
| 5,823,182 A | 10/1998 | Van Oort |
| 6,006,747 A | 12/1999 | Eisele et al. |
| 6,065,472 A | 5/2000 | Anderson et al. |
| 6,095,153 A | 8/2000 | Kessler et al. |
| 6,481,437 B1 | 11/2002 | Pate |
| 7,186,958 B1 | 3/2007 | Nelson |
| 7,997,280 B2 | 8/2011 | Rosenthal |
| 8,488,952 B2 | 7/2013 | Landry |
| 8,490,627 B2 | 7/2013 | Levin et al. |
| 8,714,150 B2 | 5/2014 | Alelov |
| 8,910,630 B2 | 12/2014 | Todd |
| 9,693,587 B2 | 7/2017 | Plojoux et al. |
| 9,775,379 B2 | 10/2017 | Davidson et al. |
| 9,943,114 B2 | 4/2018 | Batista |
| 10,172,390 B2 | 1/2019 | Nakano et al. |
| 10,179,215 B2 | 1/2019 | Raichman |
| 10,219,543 B2 | 3/2019 | Gill et al. |
| 10,247,443 B2 | 4/2019 | Flick |
| 10,271,578 B2 | 4/2019 | John et al. |
| 10,292,436 B2 | 5/2019 | Cirillo et al. |
| 10,328,443 B2 | 6/2019 | Ricketts et al. |
| 10,602,776 B2 | 3/2020 | Batista |
| 2004/0159322 A1 | 8/2004 | Kladders et al. |
| 2005/0063686 A1 | 3/2005 | Whittle et al. |
| 2007/0045288 A1 | 3/2007 | Nelson |
| 2007/0102013 A1 | 5/2007 | Adams et al. |
| 2008/0073558 A1 | 3/2008 | Howell et al. |
| 2009/0293888 A1 | 12/2009 | Williams et al. |
| 2009/0293892 A1 | 12/2009 | Williams et al. |
| 2010/0012118 A1 | 1/2010 | Storz |
| 2010/0059070 A1 | 3/2010 | Potter et al. |
| 2010/0078022 A1 | 4/2010 | Striebig et al. |
| 2010/0139655 A1 | 6/2010 | Genosar et al. |
| 2010/0313901 A1 | 12/2010 | Fernando et al. |
| 2011/0126848 A1 | 6/2011 | Zuber et al. |
| 2011/0192399 A1 | 8/2011 | Wilke et al. |
| 2012/0304990 A1 | 12/2012 | Todd |
| 2012/0325227 A1 | 12/2012 | Robinson et al. |
| 2013/0032145 A1 | 2/2013 | Adler et al. |
| 2013/0186392 A1 | 7/2013 | Haartsen et al. |
| 2013/0233309 A1 | 9/2013 | Todd |
| 2013/0233312 A1 | 9/2013 | Cohn |
| 2013/0255702 A1 | 10/2013 | Griffith, Jr. et al. |
| 2013/0276799 A1 | 10/2013 | Davidson et al. |
| 2014/0041655 A1 | 2/2014 | Barron et al. |
| 2014/0060554 A1 | 3/2014 | Collett et al. |
| 2014/0186015 A1 | 7/2014 | Breiwa, III et al. |
| 2014/0217197 A1 | 8/2014 | Selby et al. |
| 2014/0238423 A1 | 8/2014 | Tucker et al. |
| 2014/0299141 A1 | 10/2014 | Flick |
| 2014/0321837 A1 | 10/2014 | Flick |
| 2014/0345606 A1 | 11/2014 | Talon |
| 2014/0366609 A1 | 12/2014 | Beck et al. |
| 2015/0059747 A1 | 3/2015 | Von Schuckmann |
| 2016/0021932 A1 | 1/2016 | Silverstrini et al. |
| 2016/0057811 A1 | 2/2016 | Alarcon et al. |
| 2016/0143358 A1 | 5/2016 | Zhu |
| 2016/0295922 A1 | 10/2016 | John et al. |
| 2016/0331913 A1 | 11/2016 | Bourque |
| 2016/0338410 A1 | 11/2016 | Batista et al. |
| 2016/0345630 A1 | 12/2016 | Mironov et al. |
| 2017/0055584 A1 | 3/2017 | Blandino et al. |
| 2017/0071251 A1 | 3/2017 | Goch |
| 2017/0095624 A1 | 4/2017 | Davidson et al. |
| 2017/0119979 A1 | 5/2017 | Davidson et al. |
| 2017/0143042 A1 | 5/2017 | Batista et al. |
| 2017/0144827 A1 | 5/2017 | Batista |
| 2017/0164657 A1 | 6/2017 | Batista |
| 2017/0196262 A1 | 7/2017 | Brereton et al. |
| 2017/0311648 A1 | 11/2017 | Gill et al. |
| 2018/0007960 A1 | 1/2018 | Suzuki et al. |
| 2018/0084831 A1 | 3/2018 | Mironov |
| 2018/0104214 A1 | 4/2018 | Raichman |
| 2018/0116291 A1 | 5/2018 | Monsees et al. |
| 2018/0214645 A1 | 8/2018 | Reevell |
| 2018/0235279 A1 | 8/2018 | Wilke et al. |
| 2018/0242644 A1 | 8/2018 | Bessant et al. |
| 2018/0263286 A1 | 9/2018 | Reevell |
| 2018/0295885 A1 | 10/2018 | Rojo-Calderon et al. |
| 2018/0361334 A1 | 12/2018 | Bahabri |
| 2019/0117915 A1 | 4/2019 | Raichman |
| 2019/0208823 A1 | 7/2019 | Raichman |
| 2019/0224430 A1 | 7/2019 | Raichman |
| 2020/0229509 A1 | 7/2020 | Griscik et al. |

FOREIGN PATENT DOCUMENTS

| | | |
|---|---|---|
| CN | 104349687 A | 2/2015 |
| EP | 0525720 A1 | 2/1993 |
| EP | 1007124 A1 | 6/2000 |
| EP | 1029451 A1 | 8/2000 |
| EP | 1385595 A2 | 2/2004 |
| EP | 1504768 A1 | 2/2005 |
| EP | 3166426 A1 | 5/2017 |
| EP | 3166429 A1 | 5/2017 |
| KR | 101319228 | 10/2013 |
| RU | 2536115 C2 | 12/2014 |
| WO | WO-2003/037306 A2 | 5/2003 |
| WO | WO-2015/116934 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/005533 | 1/2016 |
| WO | WO-2016/026219 A1 | 2/2016 |
| WO | WO2019162498 A1 * | 8/2019 ............ A24F 47/00 |

OTHER PUBLICATIONS

Chinese Office Action, dated Sep. 5, 2023, issued in corresponding Chinese Patent Application No. 202180089072.6.
International Search Report and Written Opinion for PCT/US2021/060505 dated Mar. 30, 2022.
Crafty Vaporizer manual (2014).

* cited by examiner

CAPSULES WITH INTEGRATED MOUTHPIECES, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a base portion, a first cover, a second cover, an aerosol-forming substrate, and a heater. The base portion includes an engagement assembly. The first cover is engaged with the base portion via the engagement assembly. The first cover includes a first interior surface and a first exterior surface. The first interior surface defines a first recess. The second cover is engaged with the base portion and the first cover via the engagement assembly. The second cover includes a second interior surface and a second exterior surface. The second interior surface defines a second recess. The first cover is aligned with the second cover such that the first recess and the second recess collectively form a chamber. The aerosol-forming substrate is within the chamber. The heater is configured to heat the aerosol-forming substrate to generate an aerosol. The heater includes a first end section, an intermediate section, and a second end section. The heater extends from the base portion such that the intermediate section is in the chamber.

At least one embodiment relates to a heat-not-burn (HNB) aerosol-generating device. In an example embodiment, the aerosol-generating device may include a capsule and a device body. The capsule includes a housing containing an aerosol-forming substrate and a heater configured to heat the aerosol-forming substrate. The housing includes a base portion, a first cover, and a second cover. The first cover and the second cover jointly define therebetween a chamber, an aerosol channel, and an aerosol outlet. The aerosol-forming substrate is disposed in the chamber. The heater is supported by the base portion and extends into the chamber. The device body is configured to connect to the capsule. The device body includes a power source configured to supply an electric current to the heater.

At least one embodiment relates to a method of generating an aerosol. In an example embodiment, the method may include supplying an electric current to a capsule including a housing containing an aerosol-forming substrate and a heater such that the heater undergoes resistive heating. The housing includes a base portion, a first cover, and a second cover. The first cover and the second cover jointly define therebetween a chamber, an aerosol channel, and an aerosol outlet. The aerosol-forming substrate is disposed in the chamber. The heater is supported by the base portion and extends into the chamber. The method may optionally include drawing the aerosol generated by the resistive heating from the chamber and through the aerosol channel and the aerosol outlet.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
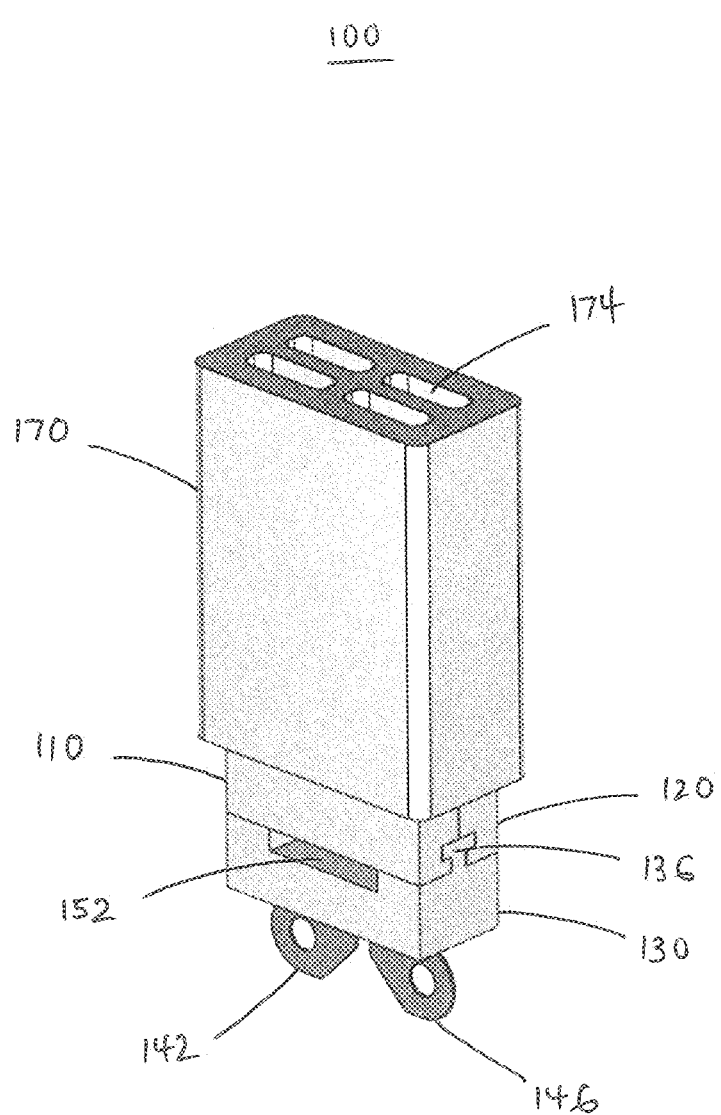
FIG. 1 is a first perspective view of a capsule for an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the terms "about" or "substantially" are used in this specification in connection with a numerical value, it is intended that the associated numerical value includes a manufacturing or operational tolerance (e.g., ±10%) around the stated numerical value. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

The processing circuitry may be hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Figure 2:
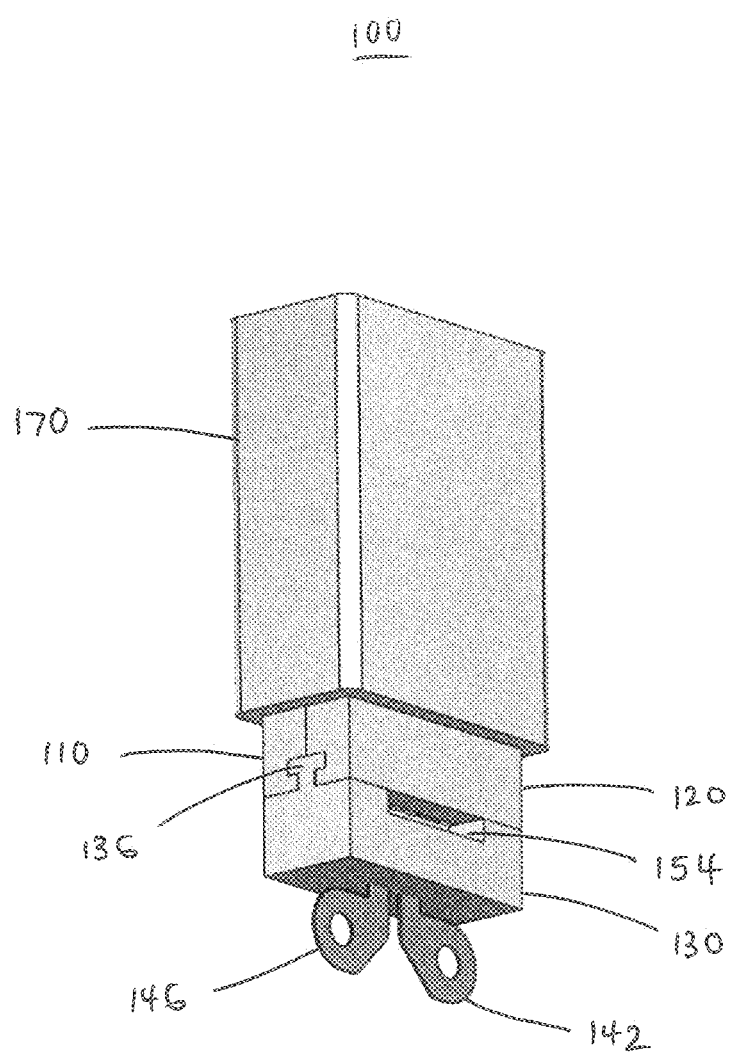
FIG. 2 is a second perspective view of the capsule of FIG. 1.

FIG. 1 is a first perspective view of a capsule for an aerosol-generating device according to an example embodiment. FIG. 2 is a second perspective view of the capsule of FIG. 1. Referring to FIGS. 1-2, a capsule 100 includes a housing configured to hold an aerosol-forming substrate and to accommodate a heater configured to heat the aerosol-forming substrate to generate an aerosol. The housing of the capsule 100 includes a base portion 130, a first cover 110, and a second cover 120. The base portion 130 includes an engagement assembly 136 configured to facilitate a connection with the first cover 110 and the second cover 120. Once connected to the base portion 130, the first cover 110 and the second cover 120 are configured to be received by an end cap 170. The end cap 170 defines at least one aerosol outlet 174. As a result, the end cap 170 may be regarded as a mouthpiece that is integrated with the housing to produce a capsule 100 that is of a 4-piece construction.

Additionally, when connected, the base portion 130 and the first cover 110 define a first air inlet 152 therebetween. Similarly, the base portion 130 and the second cover 120, when connected, define a second air inlet 154 therebetween. The first air inlet 152 and the second air inlet 154 are in fluidic communication with the aerosol outlets 174. As a result, air drawn into the first air inlet 152 and the second air inlet 154 will flow through the capsule 100 to the aerosol outlets 174. A heater is configured to extend through the base portion 130 such that the first end section 142 and the second end section 146 are visible while the intermediate section of the heater is hidden from view when the capsule 100 is assembled. The heater will be discussed in further detail in connection with subsequent drawings.

Figure 3:
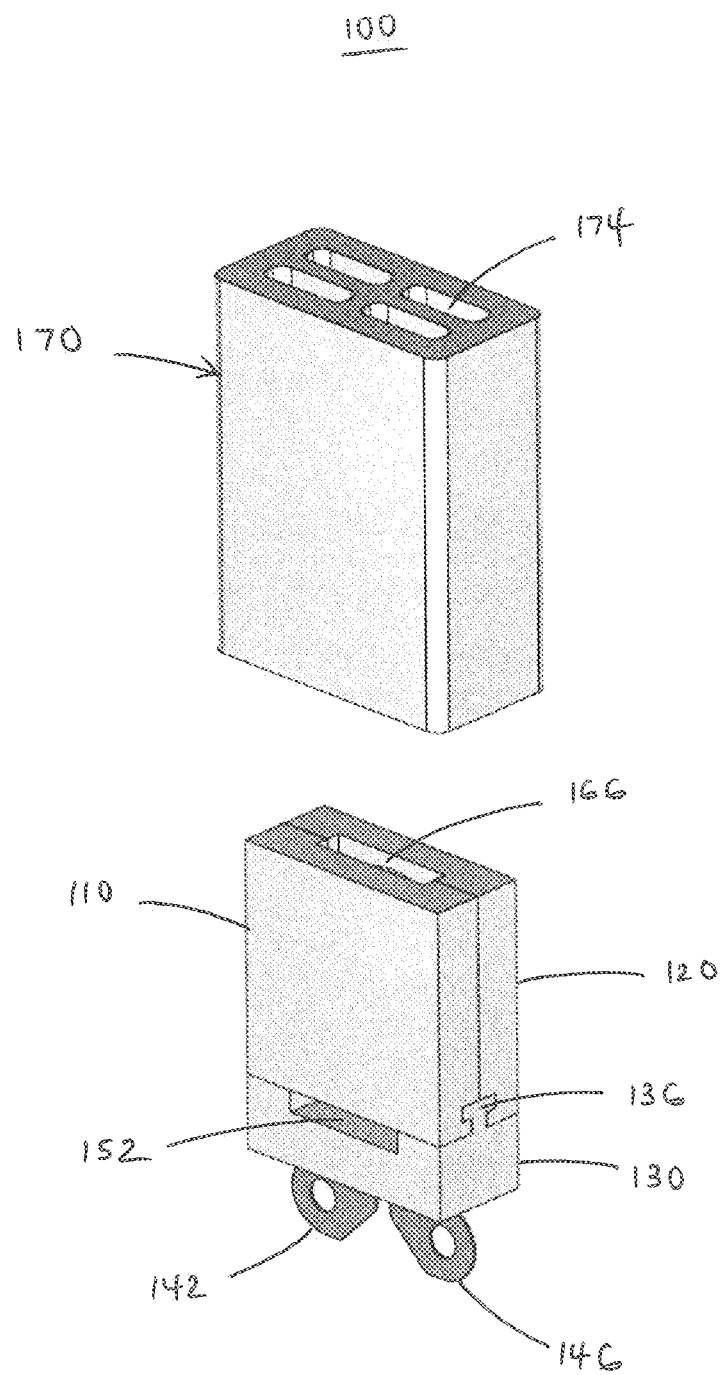
FIG. 3 is a partially exploded view of the capsule of FIG. 1.
Figure 4:
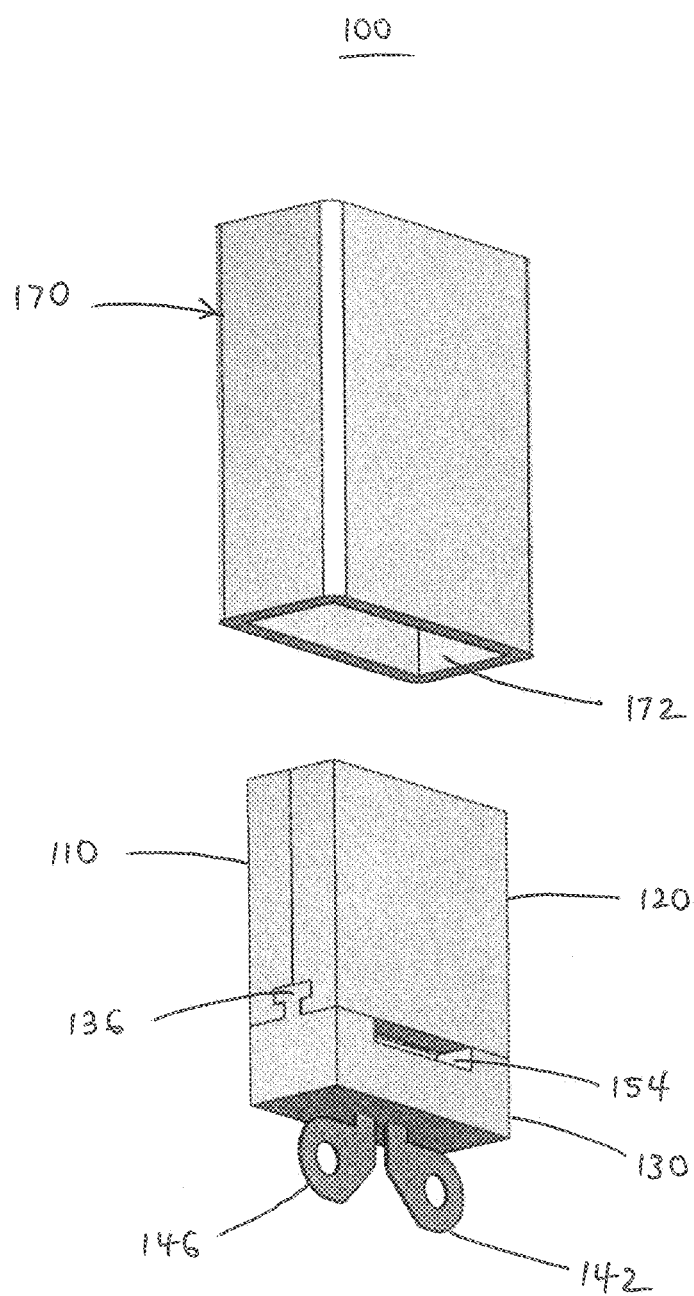
FIG. 4 is a partially exploded view of the capsule of FIG. 2.

FIG. 3 is a partially exploded view of the capsule of FIG. 1. FIG. 4 is a partially exploded view of the capsule of FIG. 2. Referring to FIGS. 3-4, the first cover 110 and the second cover 120 are configured to engage with each other and with the base portion 130 such that their adjacent surfaces are substantially flush. For instance, when engaged, the main external surface of the first cover 110 may be flush with the front surface of the base portion 130 (e.g., FIG. 3). Similarly, in another instance, the main external surface of the second cover 120 may be flush with the rear surface of the base portion 130 (e.g., FIG. 4). Additionally, in yet another instance, the opposing side surfaces of the base portion 130 may be flush with the adjoining side surfaces of the first cover 110 and the second cover 120. Furthermore, in yet another instance, the downstream end surface of the first cover 110 may be flush with the downstream end surface of the second cover 120.

When the first cover 110, the second cover 120, and the base portion 130 are coupled together, the resulting structure (e.g., housing) may have a form resembling a cuboid with a front face, an opposing rear face, a first side face, an opposing second side face, an upstream end face, and an opposing downstream end face. As used herein, "upstream" (and, conversely, "downstream") is in relation to a flow of the aerosol, and "proximal" (and, conversely, "distal") is in relation to an adult operator of the device during aerosol generation. With a form resembling a cuboid, the resulting structure (from the coupling of the first cover 110, the second cover 120, and the base portion 130) may have a rectangular cross-section. Alternatively, in other instances, the cuboid form of the resulting structure may have a square cross-section. However, it should be understood that example embodiments are not limited thereto. For instance, in lieu of a cuboid form, the resulting structure may have a form resembling a cylinder (e.g., elliptic cylinder, circular cylinder). For an elliptic cylinder, the resulting structure may have an elliptical cross-section. On the other hand, for a circular cylinder, the resulting structure may have a circular cross-section.

With regard to the cuboid form resulting from the coupling of the first cover 110, the second cover 120, and the base portion 130 as shown in the drawings, the main external surface of the first cover 110 and the front surface of the base portion 130 may be jointly regarded as the front face (e.g., which defines the first air inlet 152). Similarly, the main external surface of the second cover 120 and the rear surface of the base portion 130 may be jointly regarded as the opposing rear face (e.g., which defines the second air inlet 154). Additionally, the opposing side surfaces of the base portion 130 and the corresponding side surfaces of the first cover 110 and the second cover 120 may be jointly regarded as the first side face and the opposing second side face of the housing. Moreover, the underside or bottom of the base portion 130 may be regarded as the upstream end face (e.g., from which the first end section 142 and the second end section 146 of the heater extend). Furthermore, the downstream end surface of the first cover 110 and the corresponding downstream end surface of the second cover 120 may be jointly regarded as the downstream end face of the housing.

As shown in FIG. 3, the downstream end face of the housing defines a passageway 166. The passageway 166 is in fluidic communication with the first air inlet 152 and the second air inlet 154. As a result, when the capsule 100 is fully assembled, the air drawn into the first air inlet 152 and the second air inlet 154 will flow through the passageway 166 en route to the aerosol outlets 174. In an example embodiment, the first air inlet 152, the second air inlet 154, and the passageway 166 are dimensioned so as to be small enough to retain the aerosol-forming substrate within the housing while large enough to permit an adequate inflow of air via the first air inlet 152 and the second air inlet 154 and to permit an adequate outflow of aerosol via the passageway 166.

Although the drawings illustrate the end cap 170 as defining four aerosol outlets 174, it should be understood that example embodiments are not limited thereto. For instance, the end cap 170 may define less than four (e.g., 1-3) aerosol outlets 174. In another instance, the end cap 170 may define more than four (e.g., 5-8) aerosol outlets 174. The form of the end cap 170 may correspond to the form of the housing formed by the first cover 110, the second cover 120, and the base portion 130 (e.g., cuboid form for both the end cap 170 and the housing). Alternatively, the form of the end cap 170 may differ from the form of the housing formed by the first cover 110, the second cover 120, and the base portion 130 (e.g., cuboid form for the end cap 170 and cylindrical form for the housing or vice versa). Additionally, the aerosol outlets 174 may be arranged in a linear/sequential manner, in a radial manner, or in an array of rows and columns depending on the number of aerosol outlets 174 as well as the form and available space of the end cap 170. Furthermore, the shape of each of the aerosol outlets 174 may be circular, elongated (e.g., elliptical), polygonal (e.g., rounded rectangular), or of another suitable shape.

As shown in FIG. 4, the end cap 170 defines a cavity 172 configured to receive the first cover 110 and the second cover 120 of the housing during the assembly of the capsule 100. In an example embodiment, when the capsule 100 is assembled, the main external surfaces of the first cover 110 and the second cover 120 will interface with the corresponding main internal surfaces of the end cap 170. In lieu of (or in addition to) such an interfacial engagement, the external side surfaces of the first cover 110 and the second cover 120 may interface with the corresponding internal side surfaces of the end cap 170. Such interfacial engagements may be via an interference fit (which may also be referred to as a press fit or friction fit). However, it should be understood that other attachment techniques may also be utilized. For instance, the attachment technique may include an adhesive (e.g., tape, glue) that has been deemed food-safe or otherwise acceptable by a regulatory authority. In another instance, the attachment technique may involve ultrasonic welding.

Figure 5:
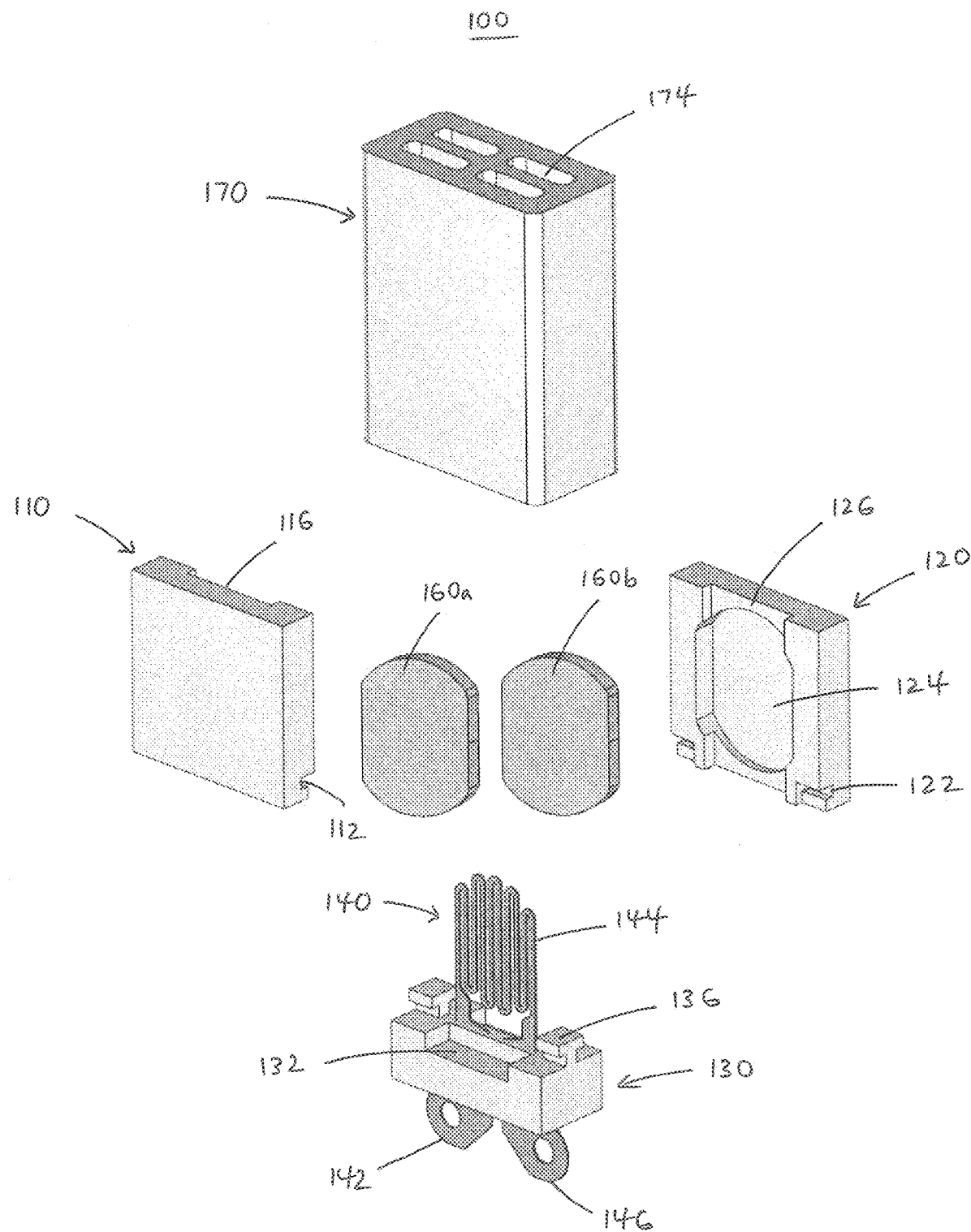
FIG. 5 is a further exploded view of the capsule of FIG. 3.
Figure 6:
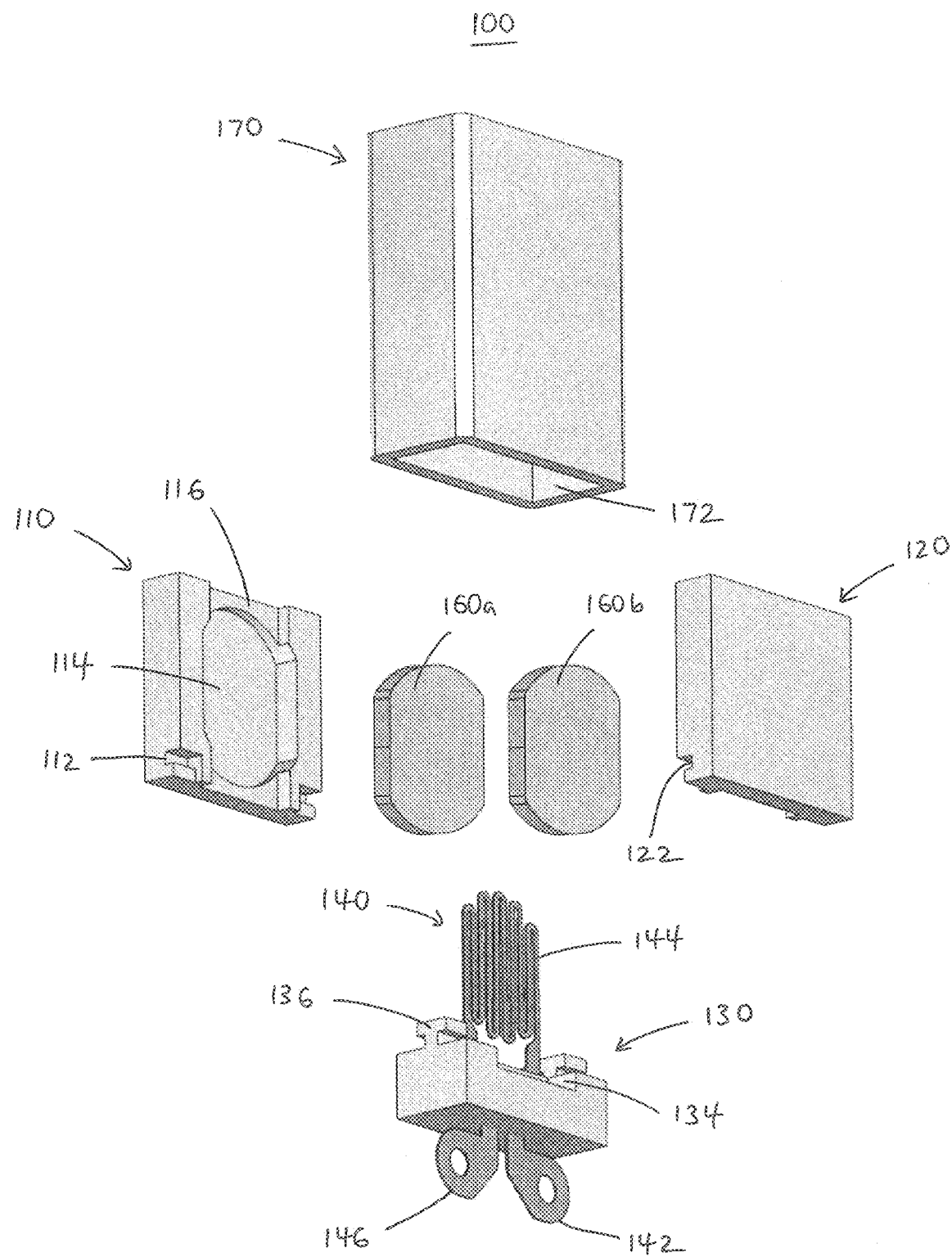
FIG. 6 is a further exploded view of the capsule of FIG. 4.

FIG. 5 is a further exploded view of the capsule of FIG. 3. FIG. 6 is a further exploded view of the capsule of FIG. 4. Referring to FIGS. 5-6, the first cover 110 defines a first notch 112, a first recess 114, and a first downstream rim 116. Similarly, the second cover 120 defines a second notch 122, a second recess 124, and a second downstream rim 126. In some instances, the first cover 110 and the second cover 120 may be identical parts. In such instances, orienting the first cover 110 and the second cover 120 to face each other for mating with the base portion 130 will result in a complementary arrangement. As a result, one part may be used interchangeably as the first cover 110 or the second cover 120, thus simplifying the method of manufacturing.

In an example embodiment, the first notch 112 may be defined as a pair of notches at the upstream corners of the first cover 110, wherein each notch may be adjacent to/exposed by the upstream end surface of the first cover 110 and also adjacent to/exposed by a side surface of the first cover 110 (e.g., FIG. 6). Likewise, the second notch 122 may be defined as a pair of notches at the upstream corners of the second cover 120, wherein each notch may be adjacent to/exposed by the upstream end surface of the second cover 120 and also adjacent to/exposed by a side surface of the second cover 120 (e.g., FIG. 5). During assembly, the first notch 112 and the second notch 122 collectively form a T-shaped notch configured to mate with the engagement assembly 136 when the first cover 110 and the second cover 120 are coupled with the base portion 130.

Additionally, the first recess 114 of the first cover 110 and the second recess 124 of the second cover 120 collectively form a chamber (e.g., chamber 164 in FIG. 7) configured to accommodate the intermediate section 144 of the heater 140 when the first cover 110 and the second cover 120 are coupled with the base portion 130. As illustrated in FIGS. 5-6, a first aerosol-forming substrate 160a and a second aerosol-forming substrate 160b may also be accommodated within the chamber so as to be in thermal contact with the intermediate section 144 of the heater 140 when the capsule 100 is assembled.

In one instance, each of the first aerosol-forming substrate 160a and the second aerosol-forming substrate 160b may be in a consolidated form (e.g., sheet, pallet, tablet) that is configured to maintain its shape so as to allow the first aerosol-forming substrate 160a and the second aerosol-forming substrate 160b to be placed in a unified manner within the first recess 114 of the first cover 110 and the second recess 124 of the second cover 120, respectively. In such an instance, the first aerosol-forming substrate 160a may be disposed on one side of the intermediate section 144 of the heater 140 (e.g., side facing the first cover 110), while the second aerosol-forming substrate 160b may be disposed on the other side of the intermediate section 144 of the heater 140 (e.g., side facing the second cover 120) so as to substantially fill the first recess 114 of the first cover 110 and the second recess 124 of the second cover 120, respectively, thereby sandwiching/embedding the intermediate section 144 of the heater 140 in between. Alternatively, one or both of the first aerosol-forming substrate 160a and the second aerosol-forming substrate 160b may be in a loose form (e.g., particles, fibers, grounds, fragments, shreds) that does not have a set shape but rather is configured to take on the shape of the first recess 114 of the first cover 110 and/or the second recess 124 of the second cover 120 when introduced.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater (e.g., heater 140 shown in FIG. 5) may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include a synthetic material. In another instance, the fibrous material may include a natural material such as a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

The first downstream rim 116 of the first cover 110 and the second downstream rim 126 of the second cover 120 jointly define the passageway 166 (e.g., FIG. 3) when the first cover 110 and the second cover 120 are coupled with the base portion 130. The first downstream rim 116 of the first cover 110 and the second downstream rim 126 of the second cover 120 are dimensioned to be small or narrow enough to retain the first aerosol-forming substrate 160a and the second aerosol-forming substrate 160b within the chamber but yet large or wide enough to permit a passage of an aerosol therethrough when the first aerosol-forming substrate 160a and the second aerosol-forming substrate 160b are heated by the heater 140.

As noted supra, the base portion 130 includes an engagement assembly 136 configured to facilitate a connection with the first cover 110 and the second cover 120 via the first notch 112 and the second notch 122, respectively. The engagement assembly 136 may be an integrally formed part of the base portion 130. In an example embodiment, the engagement assembly 136 of the base portion 130 includes a pair of mating members. The pair of mating members of the engagement assembly 136 may be adjacent to opposite edges of the base portion 130. Each of the pair of mating members of the engagement assembly 136 may have a head section and a body section, wherein the head section is wider than the body section. For instance, each of the pair of mating members of the engagement assembly 136 may have a T shape corresponding to the T-shaped notch collectively formed by the first notch 112 of the first cover 110 and the second notch 122 of the second cover 120.

As illustrated in FIGS. 5-6, the base portion 130 defines a first indentation 132 and a second indentation 134. As a result, when assembled, the surface of the base portion 130 defining the first indentation 132 and a corresponding surface of the first cover 110 jointly define the first air inlet 152 (e.g., FIG. 3). Similarly, the surface of the base portion 130 defining the second indentation 134 and a corresponding surface of the second cover 120 jointly define the second air inlet 154 (e.g., FIG. 4). The first air inlet 152 and the second air inlet 154 are in fluidic communication with the chamber (e.g., chamber 164 in FIG. 7) where the first aerosol-forming substrate 160a and the second aerosol-forming substrate 160b are disposed along with the intermediate section 144 of the heater 140.

A sheet material may be cut or otherwise processed (e.g., stamping, electrochemical etching, die cutting, laser cutting) to produce the heater 140. The sheet material may be formed of one or more conductors configured to undergo Joule heating (which is also known as ohmic/resistive heating). Suitable conductors for the sheet material include an iron-based alloy (e.g., stainless steel, iron aluminides), a nickel-based alloy (e.g., nichrome), and/or a ceramic (e.g., ceramic coated with metal). For instance, the stainless steel may be a type known in the art as SS316L, although example embodiments are not limited thereto. The sheet material may have a thickness of about 0.1-0.3 mm (e.g., 0.15-0.25 mm).

The heater 140 has a first end section 142, an intermediate section 144, and a second end section 146. The first end section 142 and the second end section 146 are configured to receive an electric current from a power source during an activation of the heater 140. When the heater 140 is activated (e.g., so as to undergo Joule heating), the temperature of the first aerosol-forming substrate 160a and the second aerosol-forming substrate 160b may increase, and an aerosol may be generated and drawn or otherwise released through the aerosol outlets 174 of the capsule 100. The first end section 142 and the second end section 146 may each define an aperture to facilitate an electrical connection with the power source, although example embodiments are not limited thereto. Additionally, because the heater 140 may be produced from a sheet material, the first end section 142, the second end section 146, and the intermediate section 144 may be coplanar. Furthermore, the intermediate section 144 of the heater 140 may have a planar and winding form resembling a compressed oscillation or zigzag with a plurality of parallel segments (e.g., eight to twelve parallel segments). However, it should be understood that other forms for the intermediate section 144 of the heater 140 are also possible (e.g., spiral form, flower-like form).

In an example embodiment, the heater 140 extends through the base portion 130. In such an instance, the first end section 142 and the second end section 146 may be regarded as external segments of the heater 140 disposed on an opposite side of the base portion 130 from the engagement assembly 136. In particular, the intermediate section 144 of the heater 140 may be on the downstream side of the base portion 130, while the terminus of each of the first end section 142 and the second end section 146 may be on the upstream side of the base portion 130. During manufacturing, the heater 140 may be embedded within the base portion 130 via injection molding (e.g., insert molding, over molding). For instance, the heater 140 may be embedded such that the intermediate section 144 is between the pair of mating members of the engagement assembly 136.

Although the first end section 142 and the second end section 146 of the heater 140 are shown in the drawings as projections extending from the upstream side of the base portion 130, it should be understood that, in some example embodiments, the first end section 142 and the second end section 146 of the heater 140 may be configured so as to constitute parts of the upstream end face of the capsule 100. For instance, the exposed portions of the first end section 142 and the second end section 146 of the heater 140 may be dimensioned and oriented so as to be situated/folded against (e.g., substantially coplanar with) the underside or bottom of the base portion 130. As a result, the first end section 142 and the second end section 146 may constitute a first electrical contact pad and a second electrical contact pad, respectively, as well as parts of the upstream end face of the capsule 100.

Figure 7:
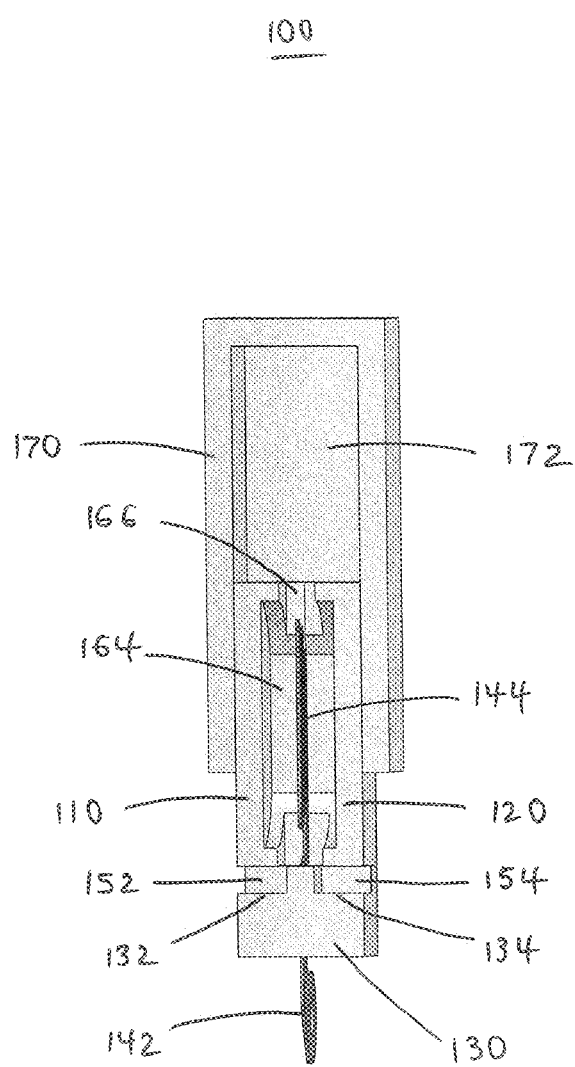
FIG. 7 is a cross-sectional view of the capsule of FIG. 1.

FIG. 7 is a cross-sectional view of the capsule of FIG. 1. Referring to FIG. 7, when the capsule 100 is assembled, the upstream portions of the first cover 110 and the second cover 120 are coupled with the base portion 130, while the downstream portions of the first cover 110 and the second cover 120 are received by the end cap 170. In addition to defining the aerosol outlets 174 (e.g., FIG. 1), the end cap 170 also defines a cavity 172. The cavity 172 is downstream from and in fluidic communication with the chamber 164 via the passageway 166. Specifically, the first air inlet 152, the second air inlet 154, the chamber 164, the passageway 166, the cavity 172, and the aerosol outlets 174 (e.g., FIG. 1) are all in fluidic communication with each other so as to permit a flow of air/aerosol therethrough.

As a result, when an electric current is supplied to the heater 140 and air is drawn into the capsule 100, the air may enter the capsule 100 through the first air inlet 152 and the second air inlet 154 (e.g., through the front face and the rear face of the capsule 100). After being drawn into the capsule 100, the air may flow longitudinally along the intermediate section 144 of the heater 140 and through the aerosol-forming substrate within the chamber 164 (e.g., the first aerosol-forming substrate 160a and the second aerosol-forming substrate 160b in FIGS. 5-6). Inside the chamber 164, volatiles are released by the aerosol-forming substrate heated by the intermediate section 144 of the heater 140 to produce an aerosol which is entrained by the air flowing through the chamber 164, the passageway 166, and the cavity 172 before exiting the capsule 100 through the aerosol outlets 174.

In an example embodiment, at least one of a filter or a flavor medium may be optionally disposed in the cavity 172 of the end cap 170. In such an instance, a filter and/or a flavor medium may be disposed in the cavity 172 within the end cap 170 so as to be downstream from the first cover 110 and the second cover 120 such that the aerosol generated within the chamber 164 passes through at least one of the filter or the flavor medium in the cavity 172 before exiting through the at least one aerosol outlet 174. The filter may reduce or prevent particles from the aerosol-forming substrate from being inadvertently drawn from the capsule 100, while the flavor medium may release a flavorant when the aerosol passes therethrough so as to impart the aerosol with a desired flavor. The flavorant may be the same as described above in connection with the aerosol-forming substrate. Furthermore, the filter and/or the flavor medium may have a consolidated form or a loose form as described supra in connection with the aerosol-forming substrate.

Figure 8:
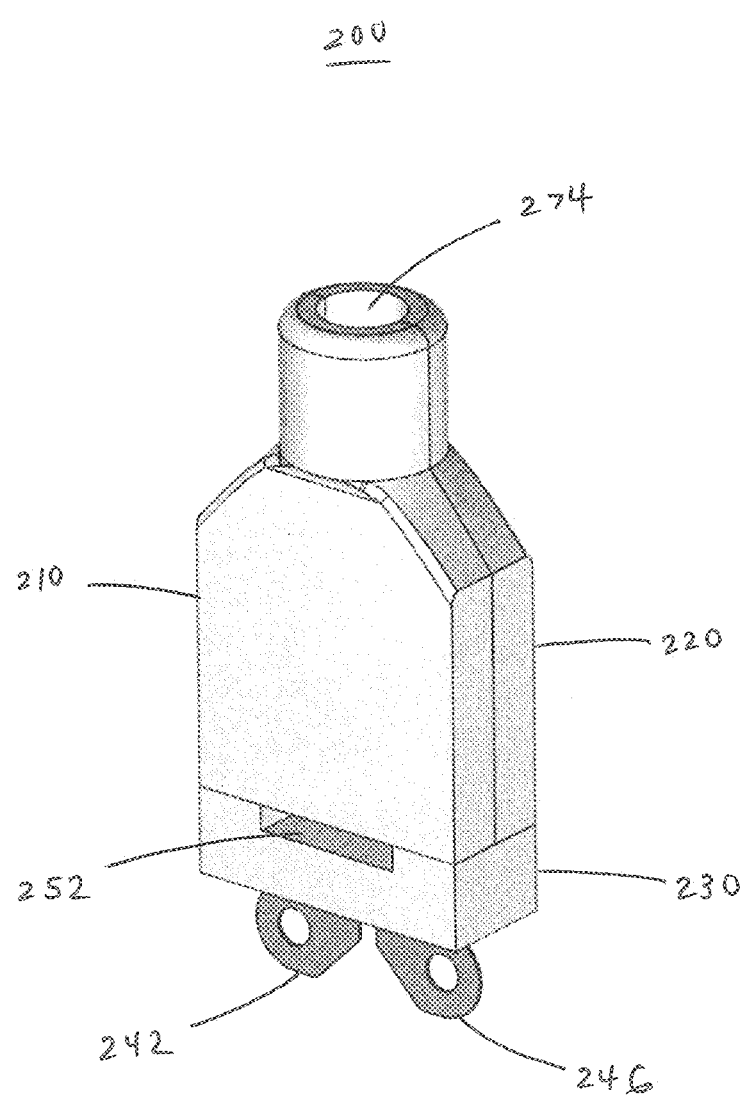
FIG. 8 is a first perspective view of another capsule for an aerosol-generating device according to an example embodiment.
Figure 9:
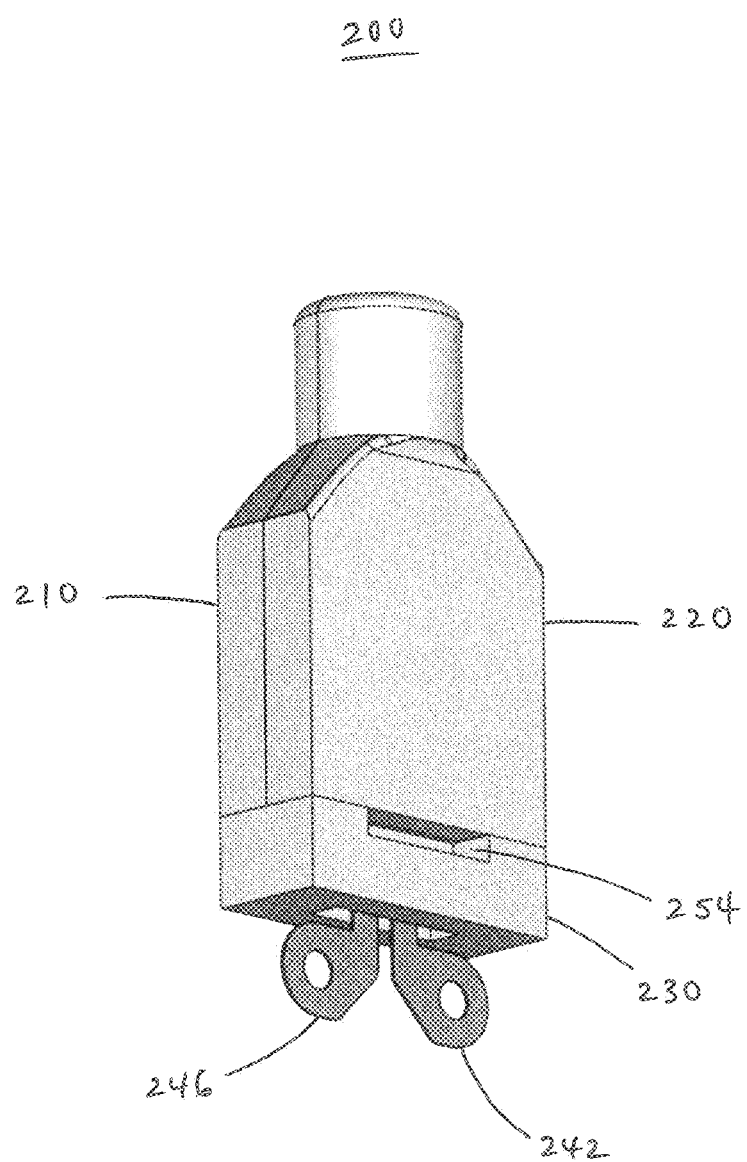
FIG. 9 is a second perspective view of the capsule of FIG. 8.

FIG. 8 is a first perspective view of another capsule for an aerosol-generating device according to an example embodiment. FIG. 9 is a second perspective view of the capsule of FIG. 8. Referring to FIGS. 8-9, a capsule 200 includes a housing configured to hold an aerosol-forming substrate and to accommodate a heater configured to heat the aerosol-forming substrate to generate an aerosol. The housing of the capsule 200 includes a base portion 230, a first cover 210, and a second cover 220. The base portion 230 includes an engagement assembly (e.g., engagement assembly 236 in FIG. 10) configured to facilitate a connection with the first cover 210 and the second cover 220. Once connected to the base portion 230, the first cover 210 and the second cover 220 jointly define an aerosol outlet 274 therebetween. As a result, the capsule 200 may be regarded as one that is of a 3-piece construction.

Additionally, when connected, the base portion 230 and the first cover 210 define a first air inlet 252 therebetween. Similarly, the base portion 230 and the second cover 220, when connected, define a second air inlet 254 therebetween. The first air inlet 252 and the second air inlet 254 are in fluidic communication with the aerosol outlet 274. As a result, air drawn into the first air inlet 252 and the second air inlet 254 will flow through the capsule 200 to the aerosol outlet 274. In an example embodiment, the downstream sector of the capsule 200 may taper to a mouth end (e.g., cylindrical end) defining the aerosol outlet 274. A heater is configured to extend through the base portion 230 such that the first end section 242 and the second end section 246 are visible while the intermediate section of the heater is hidden from view when the capsule 200 is assembled. The heater will be discussed in further detail in connection with subsequent drawings.

Although the drawings illustrate the aerosol outlet 274 as a single outlet, it should be understood that example embodiments are not limited thereto. For instance, the aerosol outlet 274 may be defined as a plurality of outlets (e.g., 2-4 outlets). The aerosol outlet 274 may be defined by the first cover 210 and the second cover 220 or, alternatively, by a separate insert or end cap. Additionally, the aerosol outlet 274, when provided as a plurality of outlets, may be arranged in a linear/sequential manner, in a radial manner, or in an array of rows and columns. Furthermore, the shape of the aerosol outlet 274 (or each of the outlets when a plurality are provided) may be circular, elongated (e.g., elliptical), polygonal (e.g., rounded rectangular), or of another suitable shape.

Figure 10:
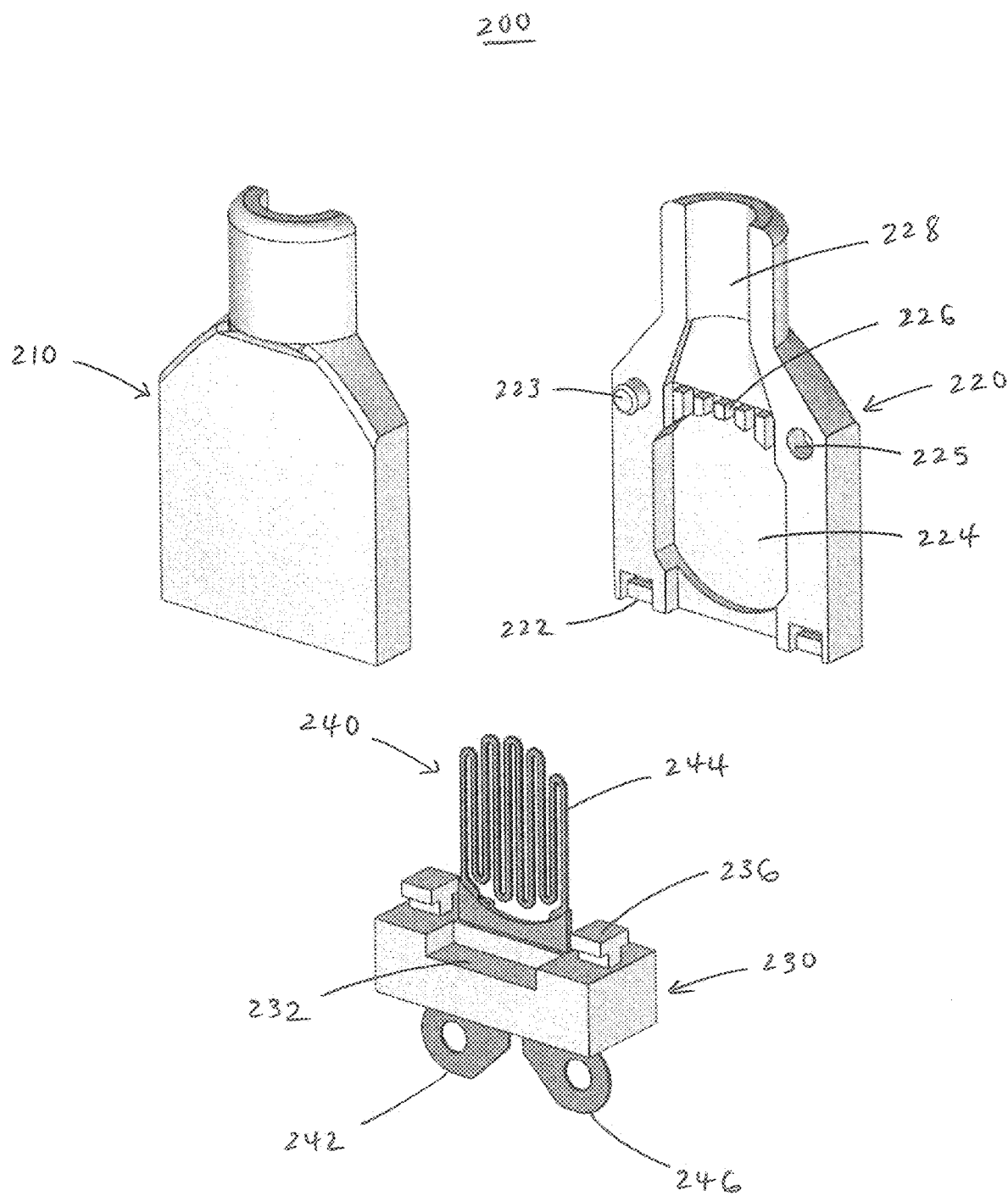
FIG. 10 is a partially exploded view of the capsule of FIG. 8.
Figure 11:
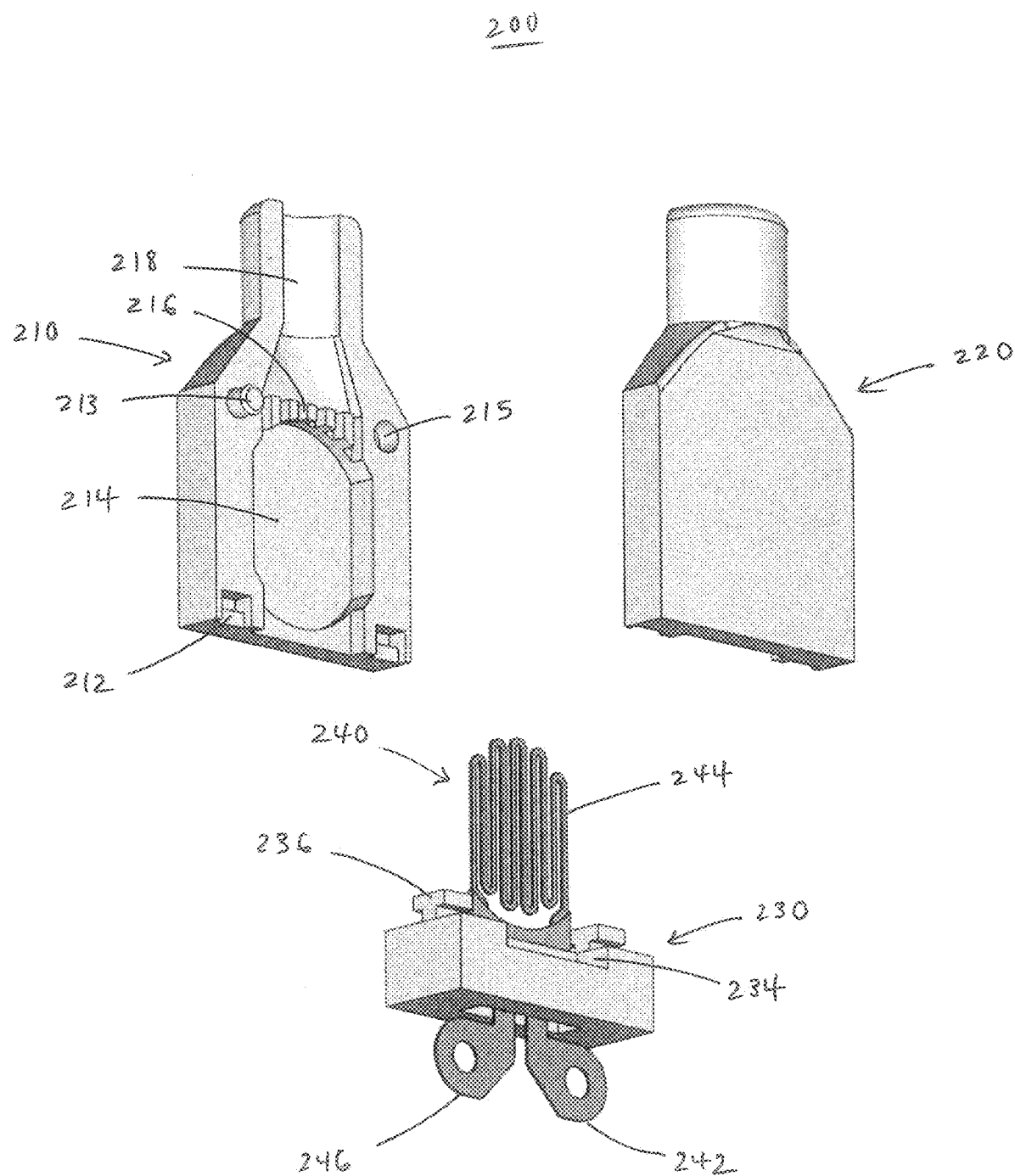
FIG. 11 is a partially exploded view of the capsule of FIG. 9.

FIG. 10 is a partially exploded view of the capsule of FIG. 8. FIG. 11 is a partially exploded view of the capsule of FIG. 9. Referring to FIGS. 10-11, the first cover 210 and the second cover 220 are configured to engage with each other and with the base portion 230 during the assembly of the capsule 200. In an example embodiment, to facilitate an engagement of the first cover 210 with the second cover 220, the first cover 210 includes a first protrusion 213 and defines a first orifice 215, while the second cover 220 includes a second protrusion 223 and defines a second orifice 225. As a result, during assembly, the first protrusion 213 of the first cover 210 will mate with the second orifice 225 of the second cover 220, while the second protrusion 223 of the second cover 220 will mate with the first orifice 215 of the first cover 210. The resulting engagement between the first cover 210 and the second cover 220 may be via an interference fit.

As illustrated, the first cover 210 also defines one or more of a first notch 212, a first recess 214, a first groove 216, and a first channel 218. Similarly, the second cover 220 defines one or more of a second notch 222, a second recess 224, a second groove 226, and a second channel 228. In some instances, the first cover 210 and the second cover 220 may be identical parts. In such instances, orienting the first cover 210 and the second cover 220 to face each other for mating (as well as for coupling with the base portion 230) will result in a complementary arrangement. As a result, one part may be used interchangeably as the first cover 210 or the second cover 220, thus simplifying the method of manufacturing.

When the capsule 200 is assembled, the first recess 214 of the first cover 210 and the second recess 224 of the second cover 220 collectively form a chamber 264 (e.g., FIG. 12) configured to accommodate both an aerosol-forming substrate and an intermediate section 244 of the heater 240. Additionally, the first interior surface of the first cover 210 further defines a first channel 218 downstream from the first recess 214, and the second interior surface of the second cover 220 further defines a second channel 228 downstream from the second recess 224. The first channel 218 and the second channel 228 are configured to collectively form an aerosol channel 268 (e.g., FIG. 12). Moreover, the first interior surface of the first cover 210 further defines first grooves 216 connecting the first recess 214 to the first channel 218, and the second interior surface of the second cover 220 further defines second grooves 226 connecting the second recess 224 to the second channel 228. The first grooves 216 and the second grooves 226 are aligned and dimensioned so as to collectively form passageways 266 (e.g., FIG. 12) configured to retain the aerosol-forming substrate within the chamber 264 while allowing the aerosol generated to pass through to the aerosol channel 268. The number of passageways 266 may range from four to eight (e.g., six), although example embodiments are not limited thereto.

The first notch 212 in the first cover 210 may be defined as a pair of notches at the upstream corners of the first cover 210, wherein each notch may be adjacent to/exposed by the upstream end surface of the first cover 210 while bounded/obscured by a corresponding side surface of the first cover 210 (e.g., FIG. 11). Likewise, the second notch 222 may be defined as a pair of notches at the upstream corners of the second cover 220, wherein each notch may be adjacent to/exposed by the upstream end surface of the second cover 220 while bounded/obscured by a corresponding side surface of the second cover 220 (e.g., FIG. 10). Alternatively, the first notch 212 and the second notch 222 may be provided as discussed in connection with the first notch 112 (e.g., FIG. 6) and the second notch 122 (e.g., FIG. 5), respectively, so as to also be exposed by a corresponding side surface of the first cover 210 and the second cover 220, respectively. During assembly, the first notch 212 and the second notch 222 collectively form a T-shaped notch configured to mate with the engagement assembly 236 when the first cover 210 and the second cover 220 are coupled with the base portion 230.

The engagement assembly 236 may be an integrally formed part of the base portion 230. In an example embodiment, the engagement assembly 236 of the base portion 230 includes a pair of mating members. The pair of mating members of the engagement assembly 236 may be adjacent to and slightly spaced away from the corresponding opposite edges of the base portion 230. As a result, the engagement assembly 236 may be hidden/obscured from view by the first cover 210 and the second cover 220 when the capsule 200 is assembled. Alternatively, the pair of mating members of the engagement assembly 236 may be positioned against (e.g., flush with) the corresponding opposite edges of the base portion 230, such as that disclosed in connection with the engagement assembly 136 of capsule 100 (e.g., FIG. 5). In such an instance, the engagement assembly 236 will still be partially visible when the capsule 200 is assembled. Each of the pair of mating members of the engagement assembly 236 may have a head section and a body section, wherein the head section is wider than the body section. For instance, each of the pair of mating members of the engagement assembly 236 may have a T shape corresponding to the T-shaped notch collectively formed by the first notch 212 of the first cover 210 and the second notch 222 of the second cover 220.

As illustrated in FIGS. 10-11, the base portion 230 defines a first indentation 232 and a second indentation 234. As a result, when the capsule 200 is assembled, the surface of the base portion 230 defining the first indentation 232 and a corresponding surface of the first cover 210 jointly define the first air inlet 252 (e.g., FIG. 8). Similarly, the surface of the base portion 230 defining the second indentation 234 and a corresponding surface of the second cover 220 jointly define the second air inlet 254 (e.g., FIG. 9). The first air inlet 252 and the second air inlet 254 are in fluidic communication with the chamber (e.g., chamber 264 in FIG. 12) where the aerosol-forming substrate is disposed along with the intermediate section 244 of the heater 240. The aerosol-forming substrate (not illustrated) for the capsule 200 may be as described in connection with any of the forms/formats for the first aerosol-forming substrate 160a and/or the second aerosol-forming substrate 160b of the capsule 100 (e.g., FIG. 5). As a result, the relevant disclosures above with regard to aerosol-forming substrates should be understood to apply to this section and may not have been repeated in the interest of brevity.

A sheet material may be cut or otherwise processed (e.g., stamping, electrochemical etching, die cutting, laser cutting) to produce the heater 240. The sheet material may be formed of one or more conductors configured to undergo Joule heating (which is also known as ohmic/resistive heating). Suitable conductors for the sheet material include an iron-based alloy (e.g., stainless steel, iron aluminides), a nickel-based alloy (e.g., nichrome), and/or a ceramic (e.g., ceramic coated with metal). For instance, the stainless steel may be a type known in the art as SS316L, although example embodiments are not limited thereto. The sheet material may have a thickness of about 0.1-0.3 mm (e.g., 0.15-0.25 mm).

The heater 240 has a first end section 242, an intermediate section 244, and a second end section 246. The first end section 242 and the second end section 246 are configured to receive an electric current from a power source during an activation of the heater 240. When the heater 240 is activated (e.g., so as to undergo Joule heating), the temperature of the aerosol-forming substrate may increase, and an aerosol may be generated and drawn or otherwise released through the aerosol outlet 274 of the capsule 200. The first end section 242 and the second end section 246 may each define an aperture to facilitate an electrical connection with the power source, although example embodiments are not limited thereto. Additionally, because the heater 240 may be produced from a sheet material, the first end section 242, the second end section 246, and the intermediate section 244 may be coplanar. Furthermore, the intermediate section 244 of the heater 240 may have a planar and winding form resembling a compressed oscillation or zigzag with a plurality of parallel segments (e.g., eight to twelve parallel segments). However, it should be understood that other forms for the intermediate section 244 of the heater 240 are also possible (e.g., spiral form, flower-like form).

In an example embodiment, the heater 240 extends through the base portion 230. In such an instance, the first end section 242 and the second end section 246 may be regarded as external segments of the heater 240 disposed on an opposite side of the base portion 230 from the engagement assembly 236. In particular, the intermediate section 244 of the heater 240 may be on the downstream side of the base portion 230, while the terminus of each of the first end section 242 and the second end section 246 may be on the upstream side of the base portion 230. During manufacturing, the heater 240 may be seated within a slot extending through the base portion 230. To enhance the seating (e.g., via an interference fit), the heater 240 may be provided with a base insert which covers segments of the heater 240 between the intermediate section 244 and the terminus of each of the first end section 242 and the second end section 246. As a result, when the heater 240 is introduced through the slot in the base portion 230, the base insert will be between the heater 240 and the base portion 230 so as to create a relatively close-fit arrangement, thus allowing the base portion 230 to grip the heater 240 in a relatively secure manner. Alternatively, the heater 240 may be embedded within the base portion 230 via injection molding (e.g., insert molding, over molding). For instance, the heater 240 may be embedded such that the intermediate section 244 is between the pair of mating members of the engagement assembly 236.

Although the first end section 242 and the second end section 246 of the heater 240 are shown in the drawings as projections extending from the upstream side of the base portion 230, it should be understood that, in some example embodiments, the first end section 242 and the second end section 246 of the heater 240 may be configured so as to constitute parts of the upstream end face of the capsule 200. For instance, the exposed portions of the first end section 242 and the second end section 246 of the heater 240 may be dimensioned and oriented so as to be situated/folded against (e.g., substantially coplanar with) the underside or bottom of the base portion 230. As a result, the first end section 242 and the second end section 246 may constitute a first electrical contact pad and a second electrical contact pad, respectively, as well as parts of the upstream end face of the capsule 200.

In an example embodiment, the first cover 210 and the second cover 220 are configured to engage with each other and with the base portion 230 such that their adjacent surfaces are substantially flush. For instance, when engaged, the main external surface of the first cover 210 may be flush with the front surface of the base portion 230 (e.g., FIG. 8). Similarly, in another instance, the main external surface of the second cover 220 may be flush with the rear surface of the base portion 230 (e.g., FIG. 9). Additionally, in yet another instance, the opposing side surfaces of the base portion 230 may be flush with the adjoining side surfaces of the first cover 210 and the second cover 220. Furthermore, in yet another instance, the downstream end surface of the first cover 210 may be flush with the downstream end surface of the second cover 220.

When the first cover 210, the second cover 220, and the base portion 230 are coupled together, the resulting structure (e.g., housing) of the capsule 200 may have an upstream sector with a form resembling a cuboid with a front face, an opposing rear face, a first side face, an opposing second side face, and an upstream end face. With a cuboid form, the upstream sector of the capsule 200 may have a rectangular cross-section. Alternatively, in other instances, the cuboid form of the upstream sector of the capsule 200 may have a square cross-section. However, it should be understood that example embodiments are not limited thereto. For instance, in lieu of a cuboid form, the upstream sector of the capsule 200 may have a form resembling a cylinder (e.g., elliptic cylinder, circular cylinder). For an elliptic cylinder, the upstream sector of the capsule 200 may have an elliptical cross-section. On the other hand, for a circular cylinder, the upstream sector of the capsule 200 may have a circular cross-section.

With regard to the cuboid upstream sector resulting from the coupling of the first cover 210, the second cover 220, and the base portion 230 as shown in the drawings, the main external surface of the first cover 210 and the front surface of the base portion 230 may be jointly regarded as the front face (e.g., which defines the first air inlet 252). Similarly, the main external surface of the second cover 220 and the rear surface of the base portion 230 may be jointly regarded as the opposing rear face (e.g., which defines the second air inlet 254). Additionally, the opposing side surfaces of the base portion 230 and the corresponding side surfaces of the first cover 210 and the second cover 220 may be jointly regarded as the first side face and the opposing second side face of the housing. Moreover, the underside or bottom of the base portion 230 may be regarded as the upstream end face (e.g., from which the first end section 242 and the second end section 246 of the heater extend). As to the housing as a whole, the downstream end surface of the first cover 210 and the corresponding downstream end surface of the second cover 220 may be jointly regarded as the downstream end face.

As illustrated, the downstream sector of the capsule 200 may taper to a cylindrical end defining the aerosol outlet 274. However, it should be understood that example embodiments are not limited thereto. For instance, in lieu of a cylindrical end with a circular or elliptical cross-section, the downstream sector of the capsule 200 may taper to a polygonal end, which may be a cuboidal end with a rectangular or square cross-section. In another instance, the downstream sector of the capsule 200 may taper to a flattened end resembling a wedge, chisel, duckbill shape.

Figure 12:
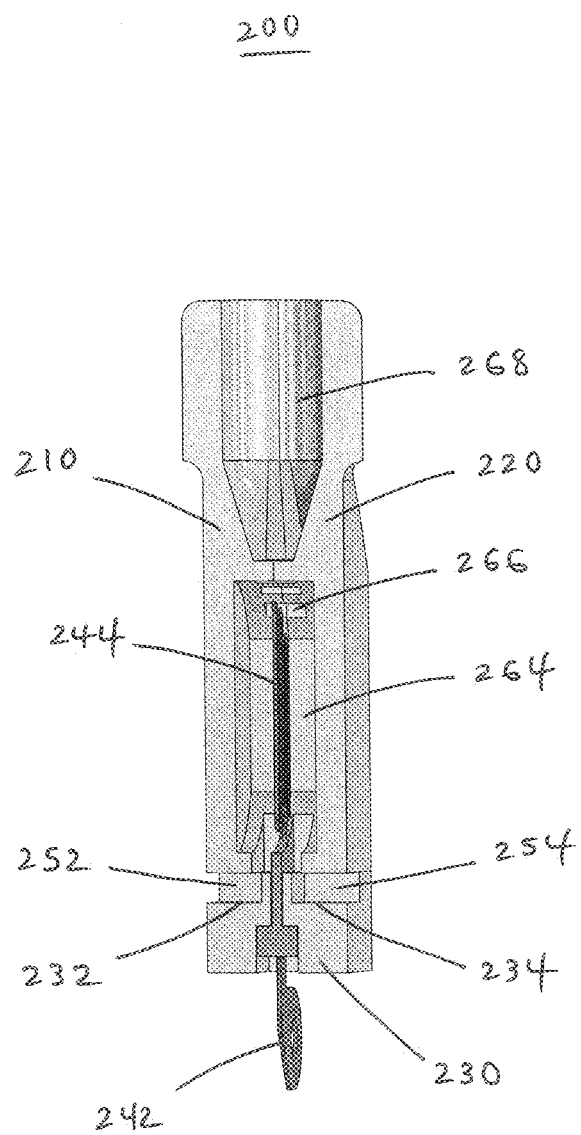
FIG. 12 is a cross-sectional view of the capsule of FIG. 8.

FIG. 12 is a cross-sectional view of the capsule of FIG. 8. Referring to FIG. 12, when the capsule 200 is assembled, the upstream portions/ends of the first cover 210 and the second cover 220 are coupled/engaged with the base portion 230, while the downstream portions/ends of the first cover 210 and the second cover 220 form a mouth end defining an aerosol channel 268 and an aerosol outlet 274 (e.g., FIG. 8). The aerosol channel 268 is downstream from and in fluidic communication with the chamber 264 via the passageways 266. Specifically, the first air inlet 252, the second air inlet 254, the chamber 264, the passageways 266, and the aerosol channel 268 are all in fluidic communication with each other so as to permit a flow of air/aerosol therethrough.

As a result, when an electric current is supplied to the heater 240 and air is drawn into the capsule 200, the air may enter the capsule 200 through the first air inlet 252 and the second air inlet 254 (e.g., through the front face and the rear face of the capsule 200). After being drawn into the capsule 200, the air may flow longitudinally along the intermediate section 244 of the heater 240 and through the aerosol-forming substrate (not illustrated) within the chamber 264. Inside the chamber 264, volatiles are released by the aerosol-forming substrate heated by the intermediate section 244 of the heater 240 to produce an aerosol which is entrained by the air flowing through the chamber 264, the passageways 266, and the aerosol channel 268 before exiting the capsule 200 through the aerosol outlet 274.

Figure 13:
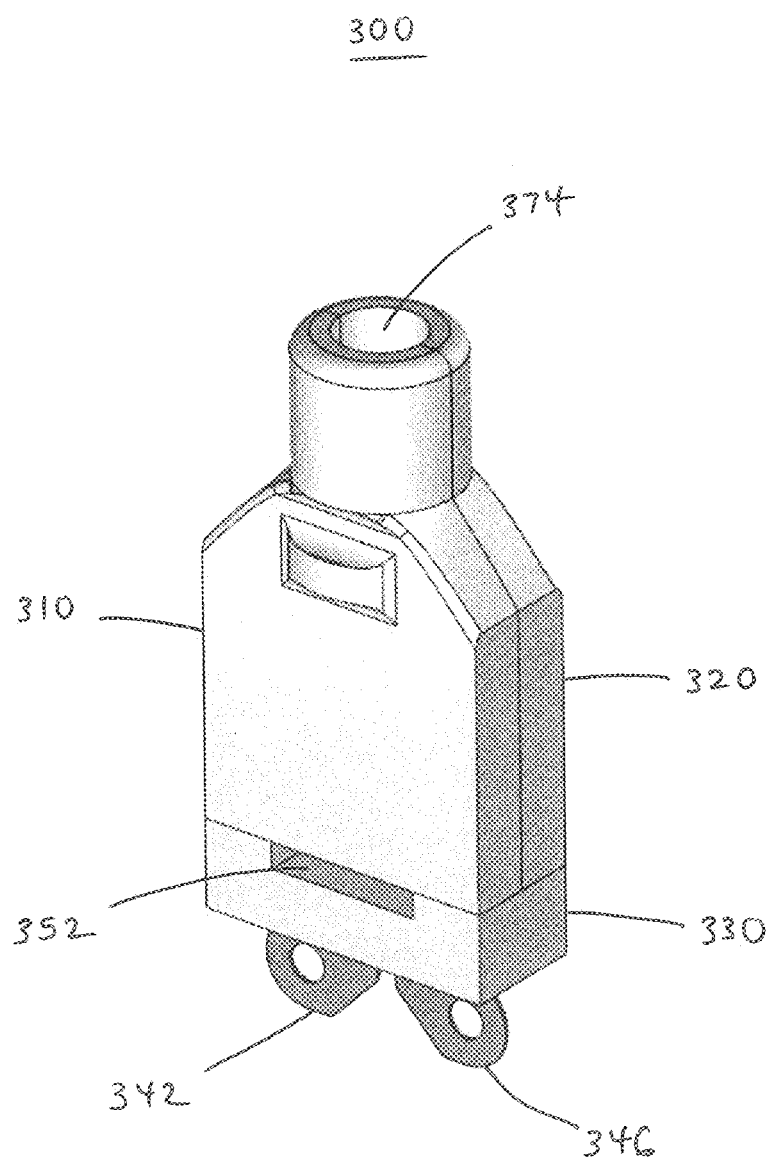
FIG. 13 is a first perspective view of another capsule for an aerosol-generating device according to an example embodiment.
Figure 14:
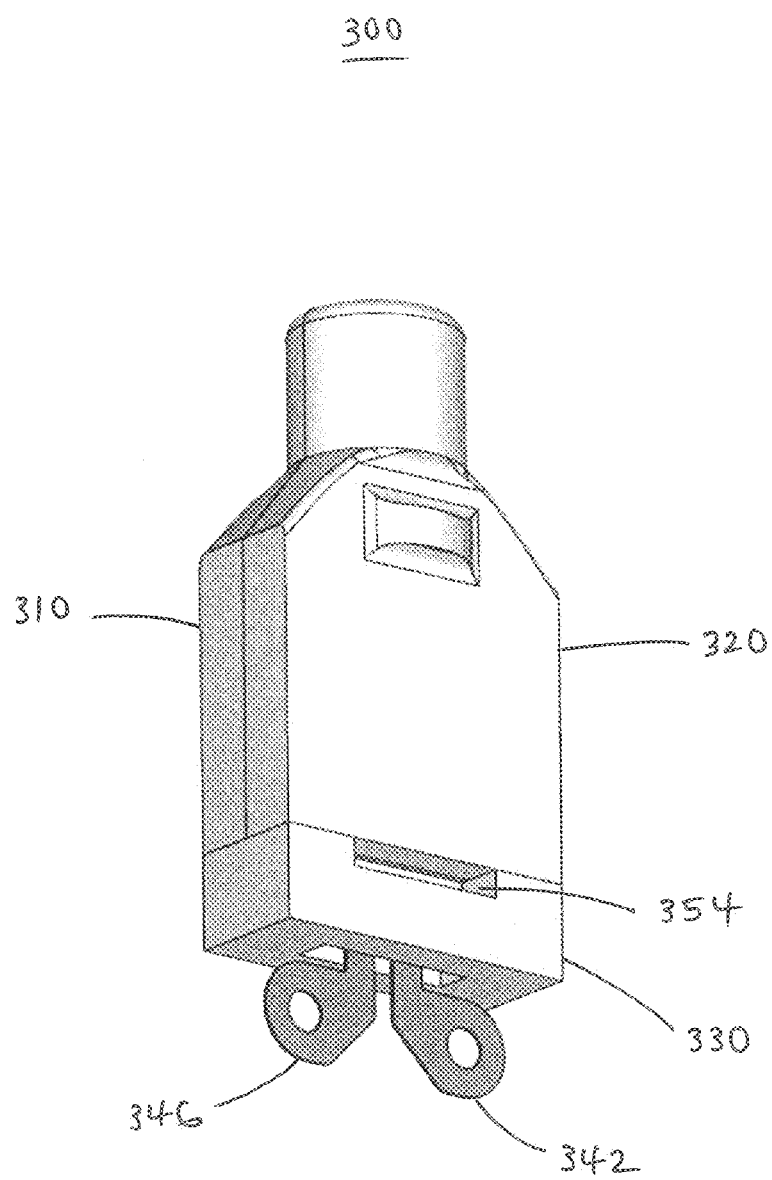
FIG. 14 is a second perspective view of the capsule of FIG. 13.

FIG. 13 is a first perspective view of another capsule for an aerosol-generating device according to an example embodiment. FIG. 14 is a second perspective view of the capsule of FIG. 13. The capsule 300 in FIGS. 13-14 may resemble the capsule 200 in FIGS. 8-9 while differing with regard to the internal slots defined by the first cover 310 and the second cover 320 as well as the corresponding external protuberances, which will be discussed in more detail herein. As a result, the relevant disclosures above of the features in common should be understood to apply to this section and may not have been repeated in the interest of brevity.

The capsule 300 includes a housing configured to hold an aerosol-forming substrate as described herein and to accommodate a heater configured to heat the aerosol-forming substrate to generate an aerosol. The housing of the capsule 300 includes a base portion 330, a first cover 310, and a second cover 320. The base portion 330 includes an engagement assembly (e.g., engagement assembly 336 in FIG. 15) configured to facilitate a connection with the first cover 310 and the second cover 320. Once connected to the base portion 330, the first cover 310 and the second cover 320 jointly define an aerosol outlet 374 therebetween. As a result, the capsule 300 may be regarded as one that is of a 3-piece construction.

Additionally, when connected, the base portion 330 and the first cover 310 define a first air inlet 352 therebetween. Similarly, the base portion 330 and the second cover 320, when connected, define a second air inlet 354 therebetween. The first air inlet 352 and the second air inlet 354 are in fluidic communication with the aerosol outlet 374. As a result, air drawn into the first air inlet 352 and the second air inlet 354 will flow through the capsule 300 to the aerosol outlet 374. In an example embodiment, the downstream sector of the capsule 300 may taper to a mouth end (e.g., cylindrical end) defining the aerosol outlet 374. A heater is configured to extend through the base portion 330 such that the first end section 342 and the second end section 346 are visible while the intermediate section 344 of the heater 340 (e.g., FIG. 15) is hidden from view when the capsule 300 is assembled. The aerosol outlet 374, the first air inlet 352, the second air inlet 354, the base portion 330, the first end section 342, and the second end section 346 in FIGS. 13-14 may be the same as described in connection with the aerosol outlet 274, the first air inlet 252, the second air inlet 254, the base portion 230, the first end section 242, and the second end section 246 in FIGS. 8-9. As a result, the relevant disclosures above of the features in common should be understood to apply to this section and may not have been repeated in the interest of brevity.

Figure 15:
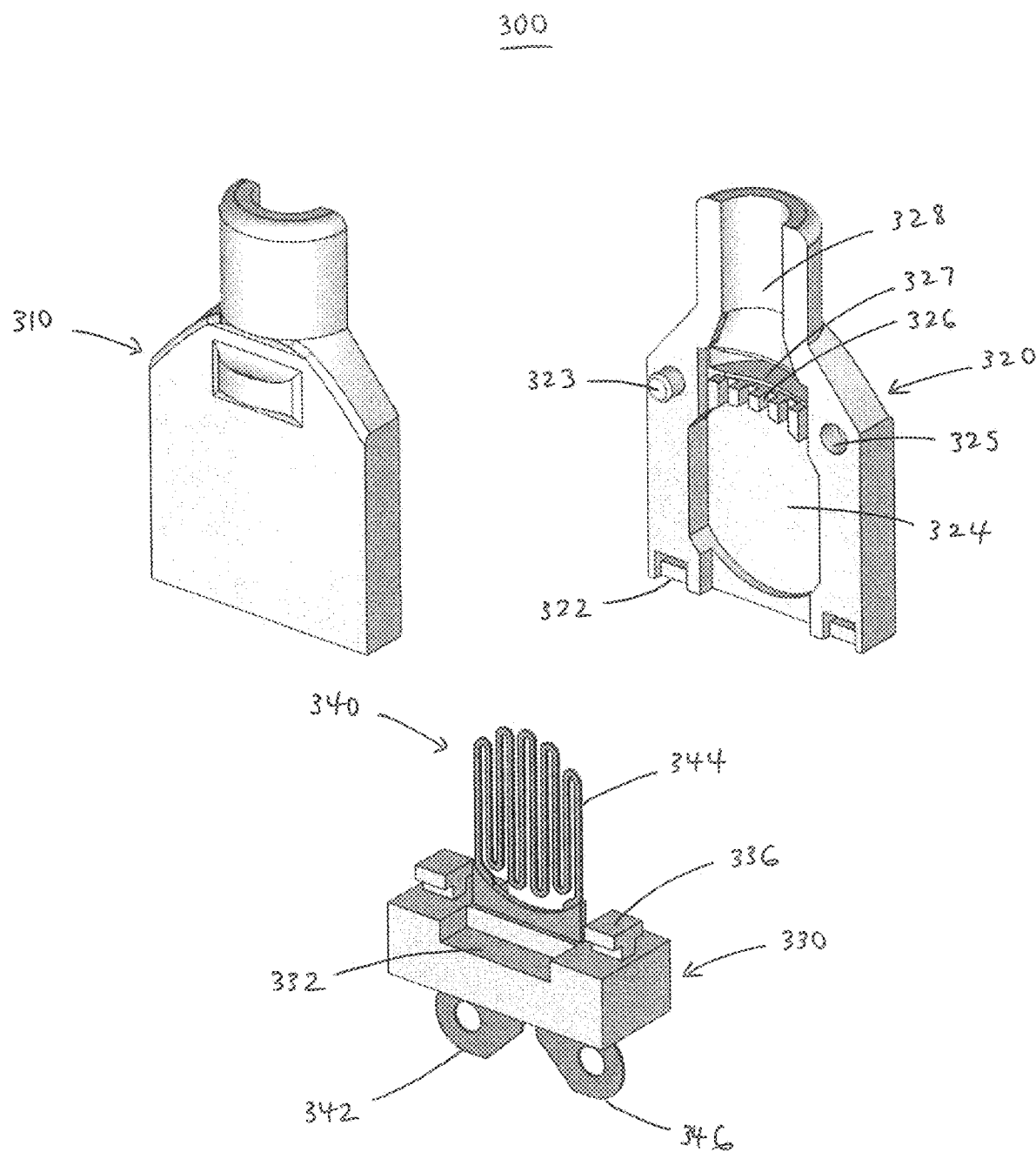
FIG. 15 is a partially exploded view of the capsule of FIG. 13.
Figure 16:
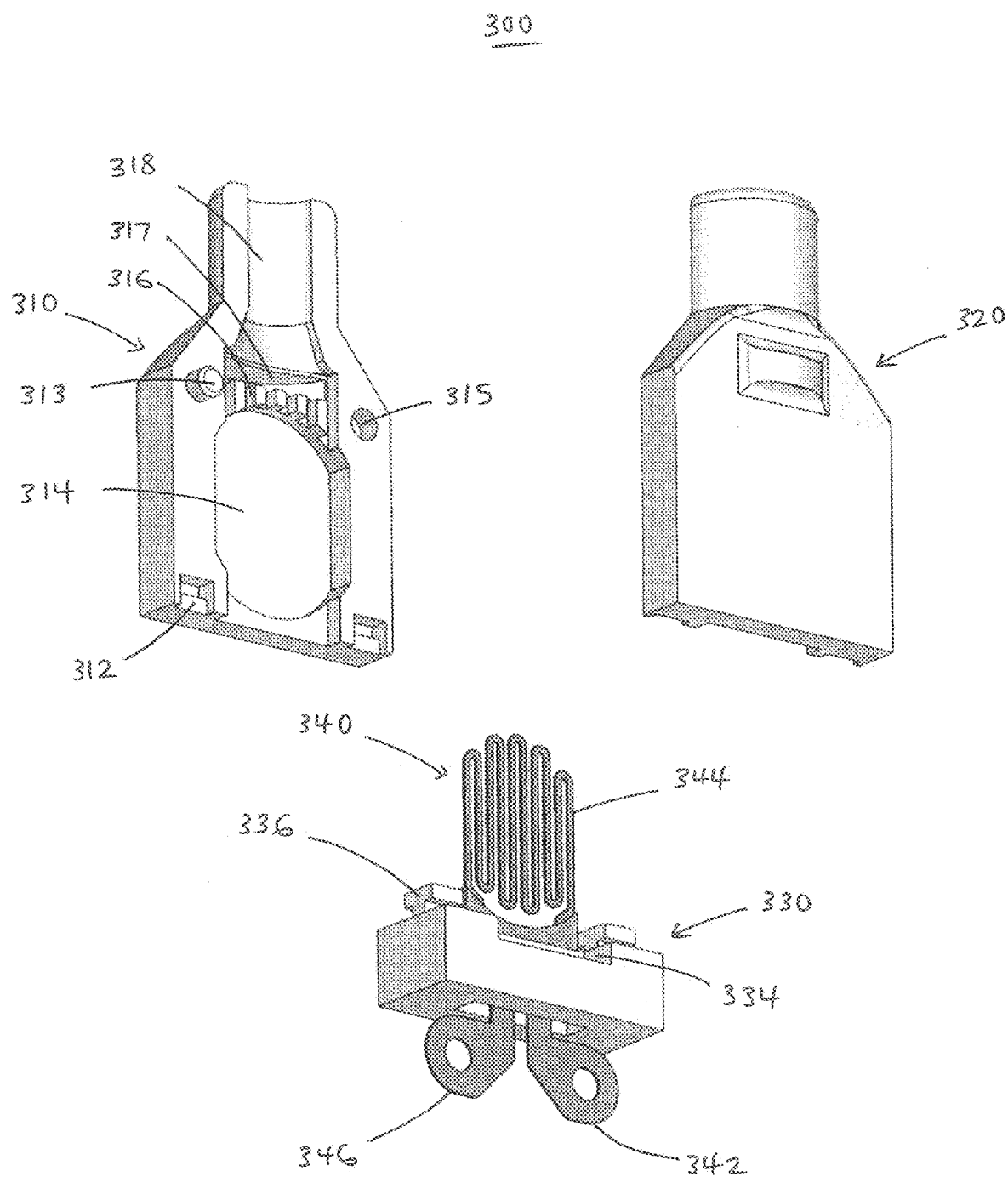
FIG. 16 is a partially exploded view of the capsule of FIG. 14.

FIG. 15 is a partially exploded view of the capsule of FIG. 13. FIG. 16 is a partially exploded view of the capsule of FIG. 14. Referring to FIGS. 15-16, the first interior surface of the first cover 310 defines a first slot 317 oriented orthogonally to the first channel 318, while the second interior surface of the second cover 320 defines a second slot 327 oriented orthogonally to the second channel 328. Each of the first slot 317 and the second slot 327 may be a half-disk-shaped concavity, although example embodiments are not limited thereto. Additionally, the first cover 310 may have a first external protuberance corresponding to the first slot 317. Similarly, the second cover 320 may have a second external protuberance corresponding to the second slot 327. Alternatively, it should be understood that the thicknesses of the first cover 310 and the second cover 320 may be increased such that the depths of the first slot 317 and the second slot 327 do not result in corresponding external protuberances in the first cover 310 and the second cover 320.

Figure 17:
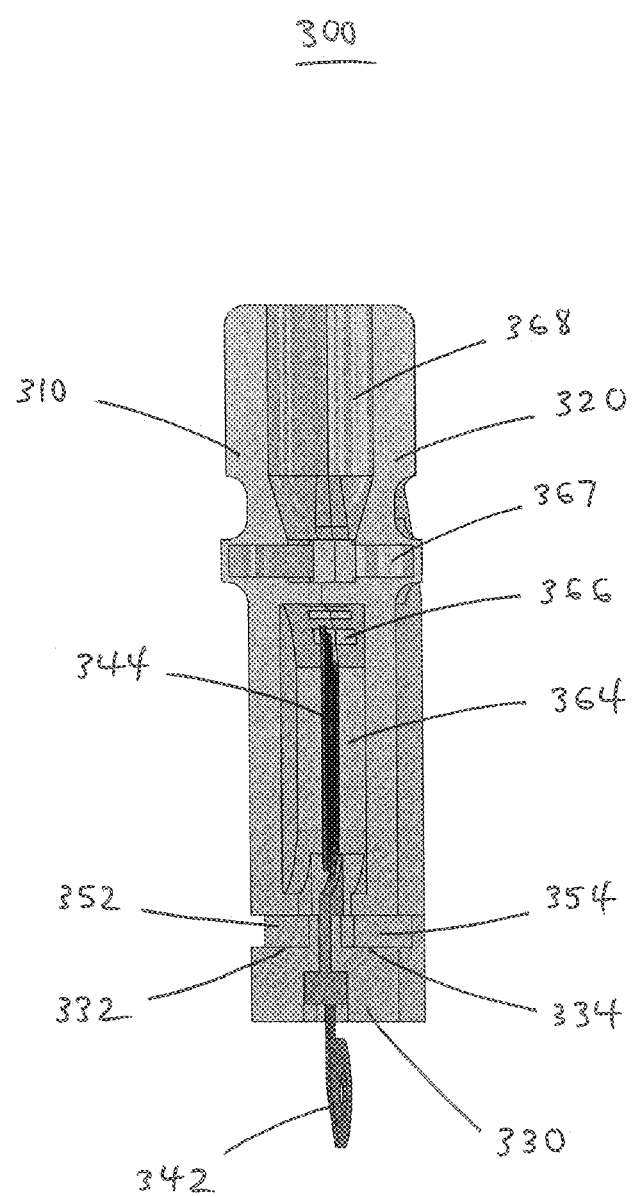
FIG. 17 is a cross-sectional view of the capsule of FIG. 13.

When the first cover 310 and the second cover 320 are engaged, the first slot 317 and the second slot 327 collectively form a compartment (e.g., compartment 367 in FIG. 17). The compartment is configured to accommodate at least one of a filter or a flavor medium as described herein. The compartment may be a disk-shaped concavity. However, it should be understood that other shaped compartments (and, thus, other shaped slots) may be provided. For instance, the compartment may be a polygon-shaped (e.g., square-shaped, hexagon-shaped, octagon-shaped) concavity configured to accommodate a similarly shaped filter and/or flavor medium.

Unless otherwise described and/or illustrated with regard to differentiating features, it should be understood that the other aspects of the first cover 310 and the second cover 320 in FIGS. 15-16 may be the same as described in connection with the first cover 210 and the second cover 220 in FIGS. 10-11. In particular, the first notch 312, the first protrusion 313, the first recess 314, the first orifice 315, the first groove 316, and the first channel 318 in FIG. 16 may be the same as described in connection with the first notch 212, the first protrusion 213, the first recess 214, the first orifice 215, the first groove 216, and the first channel 218 in FIG. 11. Similarly, the second notch 322, the second protrusion 323, the second recess 324, the second orifice 325, the second groove 326, and the second channel 328 in FIG. 15 may be the same as described in connection with the second notch 222, the second protrusion 223, the second recess 224, the second orifice 225, the second groove 226, and the second channel 228 in FIG. 10.

In some instances, the first cover 310 and the second cover 320 may be identical parts. In such instances, orienting the first cover 310 and the second cover 320 to face each other for mating (as well as for coupling with the base portion 330) will result in a complementary arrangement. As a result, one part may be used interchangeably as the first cover 310 or the second cover 320, thus simplifying the method of manufacturing.

Additionally, the base portion 330 and the heater 340 in FIGS. 15-16 may be the same as described in connection with the base portion 230 and the heater 240 in FIGS. 10-11. In particular, the first indentation 332, the second indentation 334, and the engagement assembly 336 of the base portion 330 in FIGS. 15-16 may be the same as described in connection with the first indentation 232, the second indentation 234, and the engagement assembly 236 of the base portion 230 in FIGS. 10-11. Likewise, the first end section 342, the intermediate section 344, and the second end section 346 of the heater 340 in FIGS. 15-16 may be the same as described in connection with the first end section 242, the intermediate section 244, and the second end section 246 of the heater 240 in FIGS. 10-11. As a result, the relevant disclosures above of the features in common should be understood to apply to this section and may not have been repeated in the interest of brevity.

FIG. 17 is a cross-sectional view of the capsule of FIG. 13. Referring to FIG. 17, when the capsule 300 is assembled, the upstream portions/ends of the first cover 310 and the second cover 320 are coupled/engaged with the base portion 330, while the downstream portions/ends of the first cover 310 and the second cover 320 form a mouth end defining an aerosol channel 368 and an aerosol outlet 374 (e.g., FIG. 13). The aerosol channel 368 is downstream from and in fluidic communication with the compartment 367. The compartment 367, in turn, is in fluidic communication with the chamber 364 via the passageways 366. Specifically, the first air inlet 352, the second air inlet 354, the chamber 364, the passageways 366, the compartment 367, and the aerosol channel 368 are all in fluidic communication with each other so as to permit a flow of air/aerosol therethrough.

As a result, when an electric current is supplied to the heater 340 and air is drawn into the capsule 300, the air may enter the capsule 300 through the first air inlet 352 and the second air inlet 354 (e.g., through the front face and the rear face of the capsule 300). After being drawn into the capsule 300, the air may flow longitudinally along the intermediate section 344 of the heater 340 and through the aerosol-forming substrate (not illustrated) within the chamber 364. The aerosol-forming substrate for the capsule 300 may be as described in connection with any of the forms/formats for the first aerosol-forming substrate 160a and/or the second aerosol-forming substrate 160b of the capsule 100 (e.g., FIG. 5). As a result, the relevant disclosures above with regard to aerosol-forming substrates should be understood to apply to this section and may not have been repeated in the interest of brevity.

Inside the chamber 364, volatiles are released by the aerosol-forming substrate heated by the intermediate section 344 of the heater 340 to produce an aerosol which is entrained by the air flowing through the chamber 364, the passageways 366, the compartment 367, and the aerosol channel 368 before exiting the capsule 300 through the aerosol outlet 374. Optionally, at least one of a filter or a flavor medium as described herein may be provided within the compartment 367 such that the aerosol generated in the chamber 364 passes through at least one of the filter or the flavor medium before flowing through the aerosol channel 368.

Figure 18:
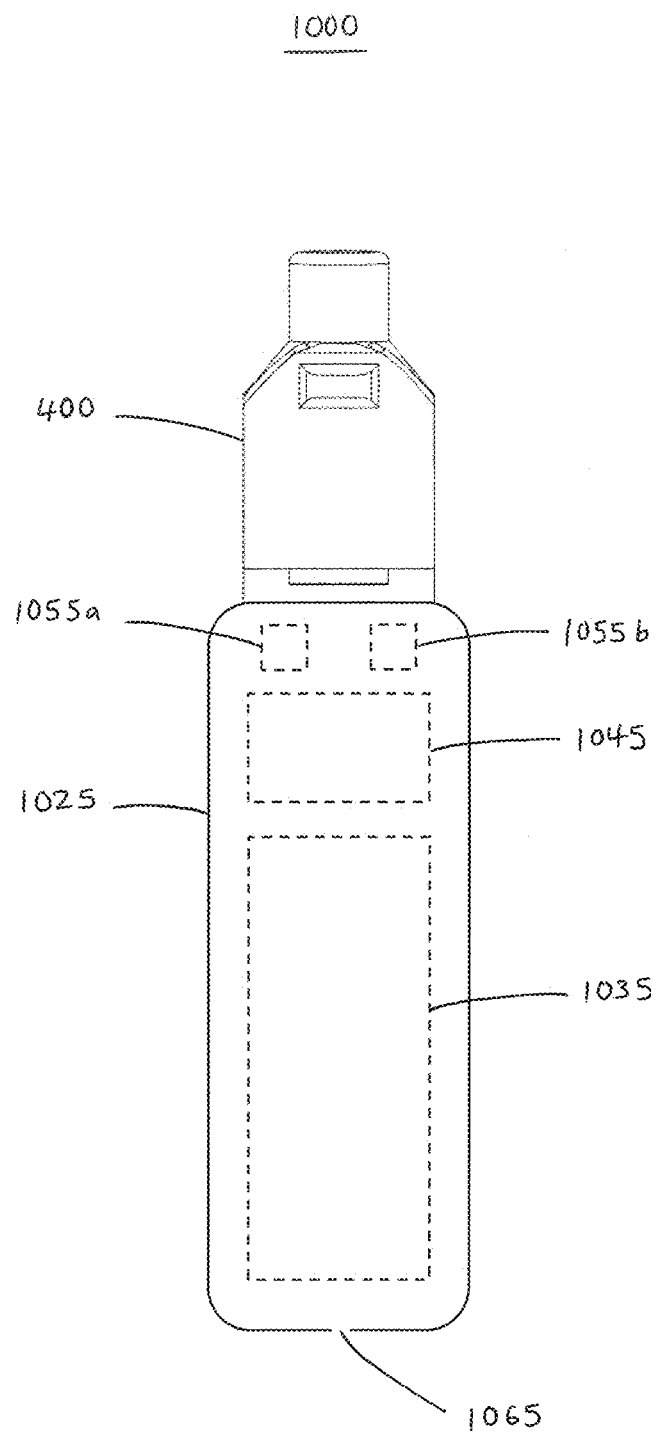
FIG. 18 is a front view of an aerosol-generating device according to an example embodiment.

FIG. 18 is a front view of an aerosol-generating device according to an example embodiment. Referring to FIG. 18, an aerosol-generating device 1000 (e.g., heat-not-burn aerosol-generating device) may include a capsule 400 and a device body 1025. In a non-limiting manner, the capsule 400 may be the same as described in connection with the capsule 100, the capsule 200, and/or the capsule 300 so as to cover various combinations of the disclosed features. For instance, the capsule 400 may include a housing containing an aerosol-forming substrate and a heater that undergoes resistive heating when activated. The housing may include a base portion, a first cover, and a second cover. The first cover and the second cover may jointly define therebetween a chamber, an aerosol channel, and an aerosol outlet, wherein the aerosol-forming substrate is disposed in the chamber. The heater is supported by the base portion and extends into the chamber.

The device body 1025 may define a socket or concavity configured to receive the capsule 400 such that the device body 1025 is mechanically and electrically engaged with the capsule 400. For instance, the socket or concavity of the device body 1025 may be configured to grip at least two opposite external surfaces (e.g., opposing sidewalls) of the capsule 400. Alternatively, the device body 1025 and/or the capsule 400 may include a magnet configured to establish a magnetic arrangement such the device body 1025 will attract and retain the capsule 400. In addition, the device body 1025 may include a first electrode 1055a and a second electrode 1055b within the socket or concavity that are configured to electrically contact a first end section and a second end section, respectively, of a heater of the capsule 400.

A power source 1035 and control circuitry 1045 may be disposed within the device body 1025 of the aerosol-generating device 1000. The power source 1035 may include one or more batteries (e.g., lithium ion rechargeable battery). When the capsule 400 is engaged with the device body 1025, the control circuitry 1045 may instruct the power source 1035 to supply an electric current to the capsule 400 via the first electrode 1055a and the second electrode 1055b of the device body 1025. The supply of current from the power source 1035 may be in response to a manual operation (e.g., button-activation) or an automatic operation (e.g., puff-activation when an incoming airflow via the air inlet 1065 is detected). As a result of the current, the aerosol-forming substrate within the capsule 400 may be heated to generate an aerosol. In addition, the change in resistance of the heater may be used by the control circuitry 1045 to monitor and control the aerosolization temperature. The aerosol generated may be drawn from the aerosol-generating device 1000 via the aerosol outlet at the mouth end of the capsule 400.

Thus, during an operation of the aerosol-generating device 1000, ambient air may be pulled into the device body 1025 via the air inlet 1065, and a method of generating an aerosol may include supplying an electric current to the capsule 400 so as to heat (e.g., via resistive heating) an aerosol-forming substrate therein. The method may additionally include drawing the aerosol generated within the chamber of the capsule 400 such that the aerosol flows through the aerosol channel and exits the aerosol outlet of the capsule 400.

Further to the non-limiting embodiments set forth herein, additional details of the substrates, capsules, devices, and methods discussed herein may also be found in U.S. application Ser. No. 16/909,131, filed Jun. 23, 2020, titled "CAPSULES INCLUDING INTERNAL HEATERS, HEAT-NOT-BURN (HNB) AEROSOL-GENERATING DEVICES, AND METHODS OF GENERATING AN AEROSOL," Atty. Dkt. No. 24000NV-000603-US; "U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL," Atty. Dkt. No. 24000NV-000522-US; and U.S. application Ser. No. 16/252,951, filed Jan. 21, 2019, titled "CAPSULES, HEAT-NOT-BURN (HNB) AEROSOL-GENERATING DEVICES, AND METHODS OF GENERATING AN AEROSOL," Atty. Dkt. No. 24000NV-000521-US, the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
   a base portion including an engagement assembly, the engagement assembly including a pair of mating members, each of the pair of mating members having a head section and a body section, the head section being wider than the body section;
   a first cover engaged with the base portion via the engagement assembly, the first cover including a first interior surface and a first exterior surface, the first interior surface defining a first recess;
   a second cover engaged with the base portion and the first cover via the engagement assembly, the second cover including a second interior surface and a second exterior surface, the second interior surface defining a second recess, the first cover aligned with the second cover such that the first recess and the second recess collectively form a chamber;
   an aerosol-forming substrate within the chamber; and
   a heater configured to heat the aerosol-forming substrate to generate an aerosol, the heater including a first end section, an intermediate section, and a second end section, the heater extending from the base portion such that the intermediate section is in the chamber.

2. The capsule of claim 1, wherein the engagement assembly is an integrally formed part of the base portion.

3. The capsule of claim 1, wherein each of the pair of mating members has a T shape.

4. The capsule of claim 1, wherein the pair of mating members are adjacent to opposite edges of the base portion.

5. The capsule of claim 1, wherein the intermediate section of the heater is between the pair of mating members.

6. The capsule of claim 1, wherein the first cover and the base portion define a first air inlet in between, the second cover and the base portion define a second air inlet in between, and the first air inlet and the second air inlet are in fluidic communication with the chamber.

7. The capsule of claim 6, wherein the base portion defines a first indentation and a second indentation as part of the first air inlet and the second air inlet, respectively.

8. The capsule of claim 1, further comprising:
an end cap configured to receive the first cover and the second cover, the end cap defining at least one aerosol outlet that is in fluidic communication with the chamber.

9. The capsule of claim 8, further comprising:
at least one of a filter or a flavor medium within the end cap and downstream from the first cover and the second cover such that the aerosol generated passes through at least one of the filter or the flavor medium before exiting through the at least one aerosol outlet.

10. The capsule of claim 1, wherein the first interior surface of the first cover further defines a first channel downstream from the first recess, the second interior surface of the second cover further defines a second channel downstream from the second recess, and the first channel and the second channel collectively form an aerosol channel.

11. The capsule of claim 10, wherein the first interior surface of the first cover further defines first grooves connecting the first recess to the first channel, and the second interior surface of the second cover further defines second grooves connecting the second recess to the second channel.

12. The capsule of claim 11, wherein the first grooves and the second grooves are aligned and dimensioned so as to retain the aerosol-forming substrate within the chamber while allowing the aerosol generated to pass through to the aerosol channel.

13. The capsule of claim 10, wherein the first interior surface of the first cover further defines a first slot oriented orthogonally to the first channel, the second interior surface of the second cover further defines a second slot oriented orthogonally to the second channel, and the first slot and the second slot collectively form a compartment.

14. The capsule of claim 13, further comprising:
at least one of a filter or a flavor medium within the compartment such that the aerosol generated in the chamber passes through at least one of the filter or the flavor medium before flowing through the aerosol channel.

15. The capsule of claim 1, wherein each of the first cover and the second cover has an upstream end and a downstream end, the upstream ends of the first cover and the second cover are engaged with the base portion, and the downstream ends of the first cover and the second cover form a tapered end defining an aerosol outlet.

16. The capsule of claim 1, wherein the aerosol-forming substrate includes a plant material.

17. The capsule of claim 16, wherein the plant material includes tobacco.

18. The capsule of claim 1, wherein the heater extends through the base portion.

19. The capsule of claim 1, wherein the first end section and the second end section are external segments of the heater disposed on an opposite side of the base portion from the engagement assembly.

20. The capsule of claim 1, wherein the intermediate section of the heater has a planar and winding form.

21. An aerosol-generating device, comprising:
a capsule including a housing containing an aerosol-forming substrate and a heater configured to heat the aerosol-forming substrate to generate an aerosol, the heater including a first end section, an intermediate section, and a second end section, the housing including
a base portion including an engagement assembly, the engagement assembly including a pair of mating members, each of the pair of mating members having a head section and a body section, the head section being wider than the body section,
a first cover engaged with the base portion via the engagement assembly, the first cover including a first interior surface and a first exterior surface, the first interior surface defining a first recess, and
a second cover engaged with the base portion and the first cover via the engagement assembly, the second cover including a second interior surface and a second exterior surface, the second interior surface defining a second recess, the first cover and the second cover jointly defining therebetween a chamber, an aerosol channel, and an aerosol outlet, the aerosol-forming substrate disposed in the chamber, the heater supported by the base portion and extending into the chamber such that the intermediate section is in the chamber; and
a device body configured to connect to the capsule, the device body including a power source configured to supply an electric current to the heater.

22. A method of generating an aerosol, comprising:
supplying an electric current to a capsule including a housing containing an aerosol-forming substrate and a heater such that the heater undergoes resistive heating, the heater including a first end section, an intermediate section, and a second end section, the housing including
a base portion including an engagement assembly, the engagement assembly including a pair of mating members, each of the pair of mating members having a head section and a body section, the head section being wider than the body section,
a first cover engaged with the base portion via the engagement assembly, the first cover including a first interior surface and a first exterior surface, the first interior surface defining a first recess, and
a second cover engaged with the base portion and the first cover via the engagement assembly, the second cover including a second interior surface and a second exterior surface, the second interior surface defining a second recess, the first cover and the second cover jointly defining therebetween a chamber, an aerosol channel, and an aerosol outlet, the aerosol-forming substrate disposed in the chamber, the heater supported by the base portion and extending into the chamber such that the intermediate section is in the chamber.

* * * * *